(12) United States Patent
Cohen et al.

(10) Patent No.: US 10,849,654 B2
(45) Date of Patent: Dec. 1, 2020

(54) TOOLS AND METHODS FOR VAGINAL ACCESS

(71) Applicant: Memic Innovative Surgery Ltd., Or-Yehuda (IL)

(72) Inventors: Dvir Cohen, Ramot-Menashe (IL); Yaron Levinson, Tel-Aviv (IL); Eyal Maimon, Kfar Edumim (IL)

(73) Assignee: Memic Innovative Surgery Ltd., Or-Yehuda (IL)

( * ) Notice: Subject to any disclaimer, the term of this patent is extended or adjusted under 35 U.S.C. 154(b) by 0 days.

(21) Appl. No.: 16/109,880

(22) Filed: Aug. 23, 2018

(65) Prior Publication Data

US 2019/0059939 A1    Feb. 28, 2019

Related U.S. Application Data

(60) Provisional application No. 62/549,097, filed on Aug. 23, 2017, provisional application No. 62/549,078, (Continued)

(51) Int. Cl.
*A61B 17/34* (2006.01)
*A61B 1/00* (2006.01)
(Continued)

(52) U.S. Cl.
CPC ...... *A61B 17/3423* (2013.01); *A61B 1/00137* (2013.01); *A61B 1/00154* (2013.01); *A61B 1/01* (2013.01); *A61B 1/313* (2013.01); *A61B 17/00234* (2013.01); *A61B 17/0218* (2013.01); *A61B 17/3421* (2013.01); *A61B 17/3494* (2013.01); *A61B 17/3496* (2013.01); *A61B 17/4241* (2013.01); *A61B 34/30* (2016.02); *A61M 29/00* (2013.01); *A61M 29/02* (2013.01); *A61B 17/3417* (2013.01); *A61B 17/42* (2013.01); *A61B 90/50* (2016.02); (Continued)

(58) Field of Classification Search
CPC ...................... A61B 17/3423; A61B 17/3421
See application file for complete search history.

(56) References Cited

U.S. PATENT DOCUMENTS 5,540,675 A    7/1996  Hasson
5,762,629 A    6/1998  Kambin
(Continued)

FOREIGN PATENT DOCUMENTS

WO    WO 2019/038770    2/2019

OTHER PUBLICATIONS

International Search Report and the Written Opinion dated Feb. 4, 2019 From the International Searching Authority Re. Application No. PCT/IL2018/050934. (20 Pages).

(Continued)

*Primary Examiner* — Andrew Yang

(57) ABSTRACT

An access port for sealing an opening of a natural orifice and supplying access to a body cavity through the natural orifice including: a sealing unit; an unobstructed single lumen cannula extending to the body cavity; a connector connecting the cannula to the sealing unit; an access opening through the sealing unit to the single lumen; a cap including a plurality of cap openings configured to seal between medical instruments inserted into the openings and the access opening.

19 Claims, 15 Drawing Sheets

Related U.S. Application Data filed on Aug. 23, 2017, provisional application No. 62/558,460, filed on Sep. 14, 2017, provisional application No. 62/558,469, filed on Sep. 14, 2017.

(51) Int. Cl.

| | | |
|---|---|---|
| *A61B 1/01* | (2006.01) | |
| *A61B 17/02* | (2006.01) | |
| *A61B 34/30* | (2016.01) | |
| *A61B 17/42* | (2006.01) | |
| *A61M 29/00* | (2006.01) | |
| *A61B 1/313* | (2006.01) | |
| *A61B 17/00* | (2006.01) | |
| *A61M 29/02* | (2006.01) | |
| *A61B 90/00* | (2016.01) | |
| *A61B 90/50* | (2016.01) | |

(52) U.S. Cl.
CPC ......... *A61B 2017/0042* (2013.01); *A61B 2017/00278* (2013.01); *A61B 2017/00398* (2013.01); *A61B 2017/00991* (2013.01); *A61B 2017/345* (2013.01); *A61B 2017/3443* (2013.01); *A61B 2017/3445* (2013.01); *A61B 2017/3452* (2013.01); *A61B 2017/3456* (2013.01); *A61B 2017/3466* (2013.01); *A61B 2017/4216* (2013.01); *A61B 2034/301* (2016.02); *A61B 2034/302* (2016.02); *A61B 2090/061* (2016.02)

(56) References Cited

U.S. PATENT DOCUMENTS

| | | | |
|---|---|---|---|
| 5,797,835 | A | 8/1998 | Green |
| 5,882,344 | A | 3/1999 | Stouder, Jr. |
| 6,156,006 | A | 12/2000 | Brosens et al. |
| 7,927,271 | B2 | 4/2011 | Dimitriou et al. |
| 8,608,652 | B2 | 12/2013 | Voegele et al. |
| 8,926,532 | B2 | 1/2015 | Barrett et al. |
| 2004/0176763 | A1 | 9/2004 | Foley et al. |
| 2004/0181231 | A1 | 9/2004 | Emstad et al. |
| 2004/0260246 | A1 | 12/2004 | Desmond |
| 2006/0069383 | A1 | 3/2006 | Bogaerts et al. |
| 2007/0118119 | A1 | 5/2007 | Hestad |
| 2008/0064921 | A1 | 3/2008 | Larkin et al. |
| 2008/0086150 | A1 | 4/2008 | Mathis et al. |
| 2008/0228213 | A1 | 9/2008 | Blakeney et al. |
| 2009/0084216 | A1 | 4/2009 | Schena et al. |
| 2009/0192520 | A1 | 7/2009 | Finlay |
| 2009/0264899 | A1 | 10/2009 | Appenrodt et al. |
| 2010/0249525 | A1* | 9/2010 | Shelton, IV ....... A61B 17/3423 600/208 |
| 2010/0268241 | A1 | 10/2010 | Flom et al. |
| 2011/0105850 | A1 | 5/2011 | Voegele et al. |
| 2011/0277775 | A1 | 11/2011 | Holop et al. |
| 2012/0130187 | A1 | 5/2012 | Okoniewski |
| 2012/0165611 | A1 | 6/2012 | Warren et al. |
| 2012/0182134 | A1 | 7/2012 | Doyle |
| 2013/0053777 | A1 | 2/2013 | Shelton, IV |
| 2013/0245381 | A1 | 9/2013 | Dang et al. |
| 2014/0039267 | A1 | 2/2014 | Seex et al. |
| 2014/0180308 | A1 | 6/2014 | von Grunberg |
| 2014/0316209 | A1 | 10/2014 | Overes et al. |
| 2015/0011978 | A1 | 1/2015 | Okamura et al. |
| 2015/0196365 | A1 | 7/2015 | Kostrzewski et al. |
| 2015/0209073 | A1 | 7/2015 | Ahn |
| 2016/0199094 | A1 | 7/2016 | Ling et al. |
| 2017/0027607 | A1 | 2/2017 | Verbeek et al. |
| 2017/0056064 | A1 | 3/2017 | Zergiebel et al. |
| 2017/0065269 | A1 | 3/2017 | Thommen et al. |
| 2017/0071685 | A1 | 3/2017 | Crawford et al. |
| 2017/0143435 | A1 | 5/2017 | Scholan et al. |
| 2017/0265947 | A1 | 9/2017 | Dyer et al. |
| 2017/0354470 | A1 | 12/2017 | Farritor et al. |
| 2018/0049824 | A1 | 2/2018 | Harris et al. |
| 2018/0070802 | A1 | 3/2018 | Becerra et al. |
| 2018/0116741 | A1 | 5/2018 | Garcia Kilroy |
| 2018/0140377 | A1 | 5/2018 | Reichenbach et al. |
| 2018/0153537 | A1 | 6/2018 | Wang et al. |
| 2018/0243048 | A1 | 8/2018 | Shan et al. |
| 2018/0318020 | A1 | 11/2018 | Thompson et al. |
| 2018/0344415 | A1 | 12/2018 | Yeung et al. |
| 2019/0059868 | A1 | 2/2019 | Cohen et al. |
| 2019/0059940 | A1 | 2/2019 | Cohen et al. |
| 2019/0059941 | A1 | 2/2019 | Cohen et al. |
| 2019/0125480 | A1 | 5/2019 | Bernstein |
| 2019/0231460 | A1 | 8/2019 | DiMaio et al. |
| 2019/0254647 | A1 | 8/2019 | Prior |
| 2019/0274665 | A1 | 9/2019 | Garcia |
| 2019/0290389 | A1 | 9/2019 | Kopp |
| 2019/0321115 | A1 | 10/2019 | Anderson et al. |
| 2020/0060724 | A1 | 2/2020 | Abboud |
| 2020/0085530 | A1 | 3/2020 | Sauer |
| 2020/0093546 | A1 | 3/2020 | Ando et al. |

OTHER PUBLICATIONS

International Preliminary Report on Patentability dated Mar. 5, 2020 From the International Bureau of WIPO Re. Application No. PCT/IL2018/050934. (12 Pages).
Restriction Official Action dated Mar. 6, 2020 From the US Patent and Trademark Office Re. U.S. Appl. No. 16/109,891. (6 pages).
Official Action dated Nov. 27, 2019 From the US Patent and Trademark Office Re. U.S. Appl. No. 16/109,893. (29 pages).
Restriction Official Action dated Nov. 25, 2019 From the US Patent and Trademark Office Re. U.S. Appl. No. 16/109,879. (9 pages).
Applied Medical Resources Corp. "Alexis® Wound Protectors/ Retractors", Applied Medical Resources Corporation, Brochure, 16 P., 2016.
Applied Medical Resources Corp. "GelPoint® Advanced Access Platforms", Applied Medical Resources Corporation, Brochure, 6 P., 2017.
Notice of Allowance dated Apr. 9, 2020 from the US Patent and Trademark Office Re. U.S. Appl. No. 16/109,893. (11 pages).
Kondo et al. "Transvaginal Natural Orifice Transluminal Endoscopic Surgery (Notes): Surgical Technique and Results," in: Advanced Gynecologic Endoscopy, Ed: Darwish. Chapter 8, 113-138, 2011.
Official Action dated Apr. 27, 2020 from the US Patent and Trademark Office Re. U.S. Appl. No. 16/109,879. (31 pages).

* cited by examiner

TOOLS AND METHODS FOR VAGINAL ACCESS

RELATED APPLICATIONS

This application claims the benefit of priority of U.S. Provisional Patent Application No. 62/549,097 filed on Aug. 23, 2017; U.S. Provisional Patent Application No. 62/549,078 filed on Aug. 23, 2017; U.S. Provisional Patent Application No. 62/558,460 filed on Sep. 14, 2017; and U.S. Provisional Patent Application No. 62/558,469 filed on Sep. 14, 2017; the contents of which are incorporated by reference as if fully set forth herein in their entirety.

This application is also a part of a set of filings which are co-filed, and co-assigned:

U.S. patent application Ser. No. 16/109,891 filed on Aug. 23, 2018 entitled "TOOLS AND METHODS FOR VAGINAL ACCESS";

PCT Patent Application No. PCT/IL2018/050934 having International Filing Date of Aug. 23, 2018 entitled "TOOLS AND METHODS FOR VAGINAL ACCESS";

Canadian Patent Application No. 3,015,084 filed on Aug. 23, 2018 entitled "TOOLS AND METHODS FOR VAGINAL ACCESS";

U.S. patent application Ser. No. 16/109,893 filed on Aug. 23, 2018 entitled "TOOLS AND METHODS FOR VAGINAL ACCESS";

Canadian Patent Application No. 3,015,089 filed on Aug. 23, 2018 entitled "TOOLS AND METHODS FOR VAGINAL ACCESS";

U.S. patent application Ser. No. 16/109,880 filed on Aug. 23, 2018 entitled "TOOLS AND METHODS FOR VAGINAL ACCESS"; and U.S. patent application Ser. No. 16/109,879 filed on Aug. 23, 2018 entitled "TOOLS AND METHODS FOR VAGINAL ACCESS";

the disclosures of which are all incorporated herein by reference.

FIELD AND BACKGROUND OF THE INVENTION

The present invention, in some embodiments thereof, relates to a minimally invasive surgery and more particularly but not exclusively to tools and methods to access a body cavity through a natural orifice and more particularly but not exclusively to culdoscopic access to the intraperitoneal space.

U.S. Pat. No. 8,608,652 appears to disclose, "A surgical method, system, kit, and various devices," . . . "for use in, among other things, vaginal entry during a natural orifice translumenal endoscopic surgical procedure. A system and/or method provide for the rapid creation of a conduit and/or multiple ports in a natural orifice, such as a patient's vagina, while accommodating anatomical variation to reduce the need to excise additional tissue from the patient."

The contents of the above applications are all incorporated by reference as if fully set forth herein in their entirety.

SUMMARY OF THE INVENTION

Following are examples of some embodiments of the invention. Features of one example may be combined with features of one or more other examples, unless expressly prohibited and form additional examples of some embodiments of the invention.

Example 1

An access port for sealing an opening of a natural orifice and supplying access to a body cavity through the natural orifice comprising:
  a sealing unit;
  an unobstructed single lumen cannula extending to said body cavity;
  a connector connecting said cannula to said sealing unit;
  an access opening through the sealing unit to said single lumen;
  a cap including a plurality of cap openings configured to seal between medical instruments inserted into the openings and said access opening.

Example 2

The access port of Example 1, wherein said connector comprises a connector lumen which defines said access opening.

Example 3

The access port of Example 2, wherein said connector lumen comprises proximal and distal openings, said proximal opening disposed proximal to a proximal face of said sealing unit, said distal opening disposed distal of a distal face of said sealing unit.

Example 4

The access portion according to any one of Examples 1-3, wherein one or both of proximal and distal openings of said connector has a flange.

Example 5

The access port according to any one of Examples 1-4, comprising an opening through said sealing unit to the natural orifice.

Example 6

The access port according to any one of Examples 1-5, wherein said natural orifice is a vagina.

Example 7

The access port of according to any one of Examples 1-6, wherein said cannula is open to an intraperitoneal cavity through said natural orifice.

Example 8

The access port according to any one of Examples 1-7, comprising a sheath extending from a proximal face of said sealing unit, through said sealing unit and through to said cannula lumen and extending within at least a portion of a length of said cannula lumen.

Example 9

The access port according to any one of Examples 8, comprising a cannula seal configured to seal one or both of a proximal opening of said cannula and a proximal opening of said sheath.

Example 10

The access port according to any one of Examples 1-8, comprising a port element describing a channel through said sealing unit and opening to said cavity.

Example 11

The access port according to any one of Examples 1-9, comprising a port element describing a channel through said sealing unit and opening into said lumen of said cannula.

Example 12

The access port of Example 11, wherein said port element includes a sheath extending from a proximal face of said sealing unit, through said cannula and extending within a least a portion of said cannula.

Example 13

The access port according to any one of Examples 1-12, wherein a transverse cross section of said single lumen has a long dimension and a short dimension; and
wherein each cap opening has a width smaller than said short dimension and the sum of widths of said plurality of cap openings is greater than said short dimension and less than said long dimension.

Example 14

The access port of Example 13, wherein said cross section of said single lumen has, in at least one dimension, a width of at least 21 mm.

Example 15

The access port according to any one of Examples 1-14, wherein a transverse cross section of said single lumen has long dimension and short dimension and at least one of said openings has a width at least 90% the short dimension.

Example 16

A kit for providing access to a cannula leading to a body cavity through a seal on a natural orifice comprising:
 a connector comprising:
 a channel with a distal opening and a proximal opening and configured to connect to
 configured to pass through said seal and attach to a cannula passing through the orifice to the body cavity, said connector having a distal opening on an inner side of said seal and a proximal opening to an outer side of said seal;
 a cap comprising a plurality of openings and sized and shaped to seal a lumen of said cannula.

Example 17

The kit of Example 16 comprising:
 a sheath sized and shaped to pass through said connector and extend within at least a portion of said cannula lumen.

Example 18

The kit of Example 17 comprising a sealing element sized and shaped to fit to one or both of said sheath and said cannula and including elastically bendable flexible portions which, when elastically relaxed, close a lumen of said sealing element to seal one or both of said sheath and said cannula.

Example 19

The kit according to any one of Examples 17-18, wherein said cap is sized and shaped to attach to one or more of a proximal opening of said cannula, a proximal opening of said sheath, and a proximal opening of said connector.

Example 20

The kit according to any one of Examples 16-19, wherein said distal opening has a cross section with a long dimension and a short dimension and wherein said long dimension is at least twice said short dimension.

Example 21

An access channel for access to a body cavity through a natural orifice comprising:
 a variable length unobstructed channel including:
 a rigid cannula having a distal opening configured to fit through an incision in a wall of the orifice;
 a rigid tubular extension for said cannula; a distal opening of said extension fitting to a proximal opening of the cannula and joining a lumen of said cannula to a lumen of said extension to form said variable length channel between said distal opening of said cannula and a proximal opening of said extension;
 said extension sliding longitudinally with respect to said cannula to extend and contract a length of said variable length channel by at least 25% of a maximal length of the channel;
 wherein a cross section of the channel has a long dimension at least twice a short dimension of said cross section.

Example 22

The access channel of Example 21, comprising:
 a seal attached to said extension shaped and sized to limit communication of pressure between said incision and an external opening of the orifice.

Example 23

The access channel according to any one of Examples 21-22, wherein said extension is attached to said seal by passing through a channel in said seal.

Example 24

The access channel according to any one of Examples 21-23, comprising:
 a handle rigidly joined to said cannula and extending proximally past said seal.

Example 25

The access channel of Example 24, wherein said handle passes through a port in said seal.

Example 26

The access channel according to any one of Examples 21-25, comprising:

a handle rigidly joined to said distal opening of said cannula and extending proximally past said proximal opening of said extension.

Example 27

The access channel according to any one of Examples 21-26, further comprising:
a dilator including:
a tapered tip for enlarging said incision; and
a body at least as long as said cannula and fitting through said channel.

Example 28

The access channel of Example 27, wherein a cross section of an outer contour of said dilator fills at least 80% of the area of the internal cross section of said cannula.

Example 29

An access channel to a body cavity through a natural orifice comprising:
a distal portion including a distal opening configured for insertion through an incision into the body cavity;
a proximal portion disposed within said natural orifice and including a proximal opening movable with respect to said distal portion;
a lumen joining said distal opening with said proximal opening; and
a handle rigidly attached to said distal portion and extending proximally past said proximal opening.

Example 30

The access channel of Example 29, wherein a cross section of the channel has a long dimension at least twice a short dimension of said cross section.

Example 31

The access channel of Example 30, comprising:
a seal attached to said proximal portion, said seal shaped and sized to limit communication of pressure between said incision and an external opening of the orifice; and
wherein said handle passes through a port element in said seal.

Example 32

The access channel according to any one of Examples 29-31, comprising:
a seal attached to said proximal portion, said seal shaped and sized to limit communication of pressure between incision and an external opening of the orifice.

Example 33

The access channel according to any one of Examples 29-32, comprising:
a dilator including a tapered tip for enlarging said incision and a body at least as long as said distal portion and fitting through said channel.

Example 34

The access channel of Example 33, wherein a cross section of said dilator fills at least 80% of the area of the internal cross sectional of said distal portion.

Example 35

A method for providing access to a body cavity through an orifice comprising:
inserting a distal portion of a cannula including a distal opening through a tissue separating said cavity from said orifice,
during said inserting, maintaining a position of a proximal portion of a cannula including a proximal opening inside said orifice with respect to one or more of said orifice and said cavity; and
inserting a tool through a lumen of said cannula, from said proximal opening to said distal opening through said tissue into said body cavity.

Example 36

The method of Example 35, comprising:
joining said proximal opening of said cannula to a distal opening of a tubular extension, a combined lumen said cannula and said extension providing communication between said distal opening of the cannula and a proximal opening of said extension; and
wherein said proximal opening of said extension is movable with respect to said distal opening of said cannula; and
wherein said inserting is through said proximal opening of said extension.

Example 37

The method of Example 36, comprising:
sealing an opening of the natural orifice around extension with a seal element.

Example 38

The method Example 37, comprising:
providing a plurality of ports from outside said seal element to said lumen of said extension.

Example 39

The method according to any one of Examples 36-37, comprising:
inserting multiple tools independently and simultaneously from outside said orifice through said combined lumen into said cavity.

Example 40

The method according to any one of Examples 35-39, comprising:
stabilizing said cannula from outside the orifice.

According to an aspect of some embodiments of the invention, there is provided an access channel for access to a body cavity through a natural orifice including: a variable length unobstructed channel including a rigid cannula having a distal opening configured to fit through an incision in a wall of the orifice; a rigid tubular extension for the cannula; a distal opening of the extension fitting to a proximal opening of the cannula and joining a lumen of the cannula to a lumen of the extension to form the variable length channel between the distal opening of the cannula and a proximal opening of the extension; the extension sliding longitudinally with respect to the cannula to extend and contract a length of the variable length channel by at least 25% of a maximal length of the channel wherein a cross section of the channel has a long dimension at least twice a short dimension of the cross section.

According to some embodiments of the invention, the access channel further includes: a seal attached to the extension shaped and sized to limit communication of pressure between incision and an external opening of the orifice.

According to some embodiments of the invention, the access channel further includes: a handle rigidly joined to the distal opening of the cannula and extending proximally past the seal.

According to some embodiments of the invention, the handle passes through a port in the seal.

According to some embodiments of the invention, the access channel of any of any further includes: a handle rigidly joined to the distal opening of the cannula and extending proximally past the proximal opening of the extension.

According to some embodiments of the invention, the access channel of any of any further includes: a dilator including a tapered tip for enlarging the incision and a body at least as long as the cannula and fitting through the channel.

According to some embodiments of the invention, a cross section of the dilator fills at least 80% of the area of the internal cross sectional of the cannula.

According to an aspect of some embodiments of the invention, there is provided an access channel to a body cavity through a natural orifice including: a distal portion including a distal opening configured for insertion through an incision into the body cavity; a proximal portion including a proximal opening movable with respect to the distal portion; a lumen joining the distal opening with the proximal opening; and a handle rigidly attached to the distal portion and extending proximally past the proximal opening.

According to some embodiments of the invention, a cross section of the channel has a long dimension at least twice a short dimension of the cross section.

According to some embodiments of the invention, the access channel further includes: a seal attached to the proximal portion, the seal shaped and sized to limit communication of pressure between incision and an external opening of the orifice and wherein the handle passes through a port in the seal.

According to some embodiments of the invention, the access channel further includes: a seal attached to the proximal portion, the seal shaped and sized to limit communication of pressure between incision and an external opening of the orifice.

According to some embodiments of the invention, the access channel of any of any further includes: a dilator including a tapered tip for enlarging the incision and a body at least as long as the distal portion and fitting through the channel.

According to some embodiments of the invention, a cross section of the dilator fills at least 80% of the area of the internal cross sectional of the distal portion.

According to an aspect of some embodiments of the invention, there is provided a method for providing access to a body cavity through an orifice, the orifice separated from including: inserting a distal portion of a cannula including a distal opening through a membrane separating the cavity from the orifice, maintaining a proximal portion of a cannula including a proximal opening inside the orifice; and inserting a tool through a lumen of the cannula, from the proximal opening to out the distal opening into the body cavity.

According to some embodiments of the invention, the method further includes: joining the proximal opening of the cannula to a distal opening of a tubular extension, a combined lumen the cannula and the extension providing communication between the distal opening of the cannula and a proximal opening of the extension and wherein the proximal opening of the extension is movable with respect to the distal opening of the cannula and wherein the inserting is through the proximal opening of the extension.

According to some embodiments of the invention, the method further includes: sealing an opening of the natural orifice around extension.

According to some embodiments of the invention, the method further includes: closing the proximal opening of the extension and providing a plurality of ports from outside the seal to the lumen of the extension.

According to some embodiments of the invention, the method further includes: inserting multiple tools independently and simultaneously from outside the orifice through the combined lumen into the cavity.

According to some embodiments of the invention, the method further includes: stabilizing the cannula from outside the orifice.

According to an aspect of some embodiments of the invention, there is provided a sealing unit for sealing an opening of a natural orifice and supplying access to a body cavity through the orifice including: a connector to an unobstructed single lumen trocar on a distal face of the sealing unit a plurality of sealable access openings through the sealing unit to the single lumen; wherein a cross section of the single lumen has long dimension and short dimension and each opening has a width smaller than the small dimension and the sum of widths of the openings is greater than the short dimension and less than the long dimension.

According to some embodiments of the invention, a cross section of the single lumen has long dimension and short dimension and at least one of the openings has a width at least 90% the short dimension.

According to some embodiments of the invention, a cross section of the single lumen has in at least one dimension a width of at least 21 mm.

According to some embodiments of the invention, the trocar is open to an intraperitoneal cavity through a natural orifice, the sealing unit further including an opening to the orifice.

According to an aspect of some embodiments of the invention, there is provided an access port for access to a body cavity through a natural orifice including: one or more ports opening to the cavity and at least one port opening to the natural orifice outside of the cavity.

According to some embodiments of the invention, the access port further includes: a seal for preserving a positive pressure in the cavity.

According to some embodiments of the invention, the access port further includes: a seal for preserving a positive pressure in the orifice.

According to some embodiments of the invention, the access port further includes: a connector connecting the one or more ports to an unobstructed single lumen trocar passing and wherein the one or more ports open to the single lumen.

According to some embodiments of the invention, a cross section of the single lumen has long dimension and short dimension and wherein each of the one or more ports has a width smaller than the small dimension and the sum of widths of the openings is greater than the short dimension and less than the long dimension.

According to some embodiments of the invention, a cross section of the single lumen has long dimension and short dimension and at least one of the one or more ports has a width at least 90% the short dimension.

According to some embodiments of the invention, a cross section of the single lumen has in at least one dimension a width of at least 21 mm.

According to an aspect of some embodiments of the invention, there is provided a kit for providing access to trocar leading to a body cavity through a seal on a natural orifice including: an adapter configured to pass through the seal and attach to a cannula passing through the orifice to the body cavity, the adapter having a distal opening on an inner side of the seal and a proximal opening to an outer side of the seal, an orifice access port configured to pass through the seal and provide access to the natural orifice outside the trocar.

According to some embodiments of the invention, the kit further includes: a least two cavity access ports separately sealable and opening through the adapter.

According to some embodiments of the invention, the kit further includes: a unitary cap closing over the adapter and the second.

According to some embodiments of the invention, the distal opening has a cross section with a long dimension and a short dimension and wherein the long dimension is at least twice the short dimension.

According to some embodiments of the invention, the long dimension is at least 21 mm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Overview

Figure 1:
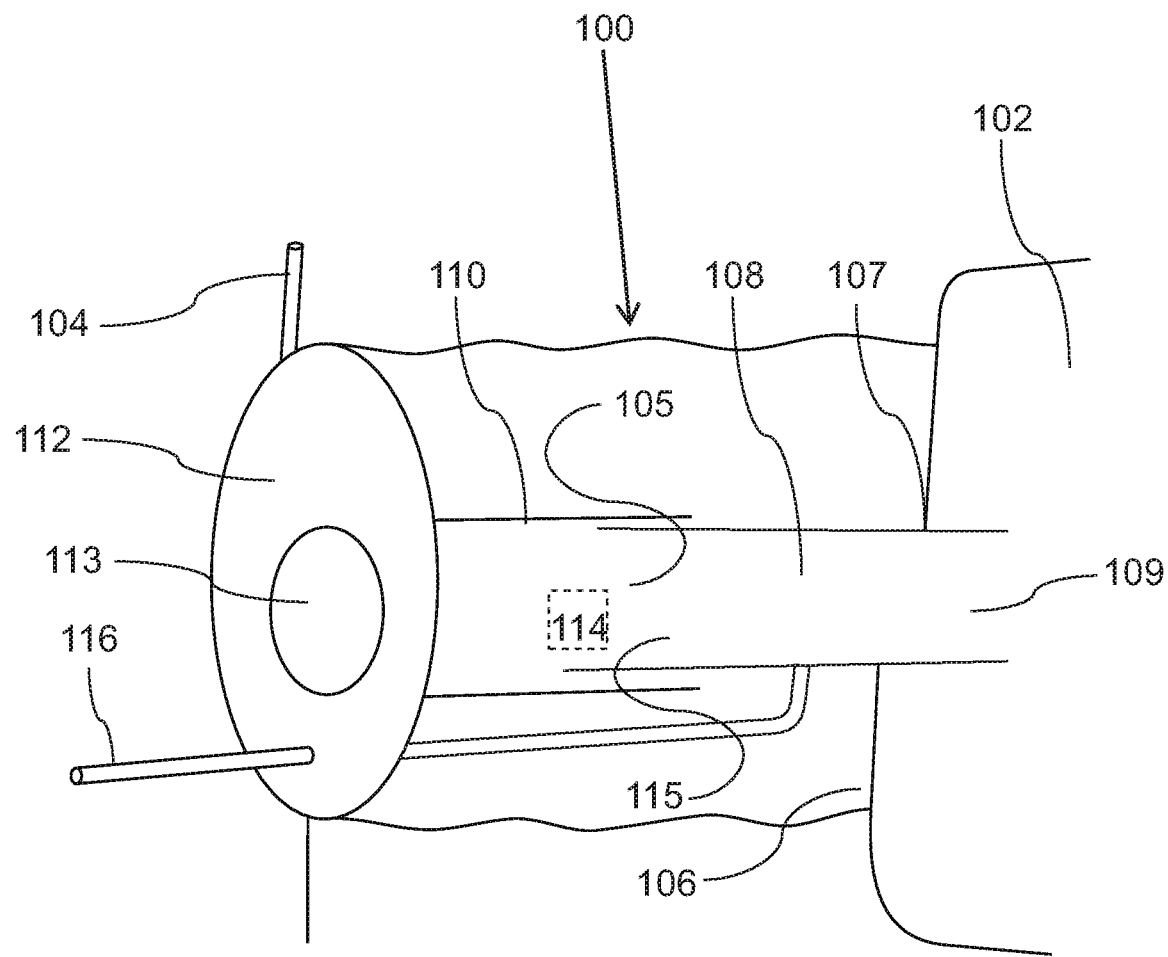
FIG. 1 is a schematic illustration of a variable length channel inserted through a natural orifice in accordance with embodiments of the current invention.

The present invention, in some embodiments thereof, relates to a minimally invasive surgery and more particularly but not exclusively to tools and methods to access a body cavity through a natural orifice and more particularly but not exclusively to culdoscopic access to the intraperitoneal space.

An aspect of some embodiments of current invention relates to a variable length channel through a natural orifice to a body cavity. In some embodiments, the channel may include a distal cannula and/or a proximal extension of the cannula. Optionally the proximal extension may move with respect to the cannula. For example, a distal opening of the cannula may be inserted into the body cavity through an incision in a wall of the orifice. Optionally, the proximal extension may be positioned to supply communication between a proximal opening of the cannula and an opening of the orifice. The length and/or position of the extension is optionally adjusted to account for the geometry of the orifice. In some embodiments, the cannula is a single lumen cannula.

In some embodiments, the cannula may include a proximally extending handle. For example, the handle may extend from the cannula out the opening of the orifice. Optionally, the handle is longer than the proximal extension of the channel. Optionally the handle is rigidly attached to the cannula. Optionally the handle may be graduated for example to indicate a depth of insertion of the cannula. In some embodiments a support may be supplied with a mount configured to hold the handle outside the subject.

In some embodiments, each section (for example the cannula and/or the extension) of the channel may be rigid. Alternatively or additionally, a cross section of each section may be fixed. For example, the outer cross section may be shaped to fit through the orifice. Optionally, the inner lumen of the channel may be adjusted to fit one or more tools, for example including a catheter and/or an endoscope. Optionally a track may be included in the channel. For example, the track may separate between tools inside the channel and/or the track may guide a tool from a proximal opening of the channel (e.g. a proximal opening of the extension) to a distal opening of the channel (e.g. a distal opening of the cannula). Alternatively or additionally one or more section of the channel may be flexible.

In some embodiments, a proximal portion of the channel moves with respect to the distal portion. In some embodiments, sections move telescopically with respect to each other. For example, relative movement may lengthen and/or shorten the channel to fit between the opening of the orifice and the incision between the orifice and the body cavity. For example, a proximal portion of the cannula may slide within a distal opening of the extension and/or a distal portion of the extension may slide within a proximal opening of the cannula. Optionally an opening of the proximal portion or the channel (e.g. the extension) is accessible from outside the orifice and/or through the opening of the orifice. For example, each section of the channel may be shorter than the orifice.

In the some embodiments, the proximal extension of the channel may be configured for sealing the orifice. For example, the proximal extension may include an adapter (for example a flange) configured far attaching to a seal of an access channel (for example a GelPOINT® cap available from Applied Medical 22872 Avenida Empresa, Rancho Santa Margarita, Calif. 92688). Optionally, the proximal extension may be stabilized in the orifice by connection to the subject, for example by connection to a seal of the orifice and/or a wound retractor. Alternatively or additionally, the extender may include a handle and/or be attached to a stabilizer outside the subject.

In some embodiments the channel may be configured for use in a vagina. For example the channel may be configured to fit through an opening of the vagina and/or to reach a Pouch of Douglas. In some embodiments, the channel is configured for use in an anus (e.g. cavity is the abdominal cavity), esophagus (e.g. cavity is a portion of the digestive tract e.g. cavity is the abdominal cavity), trachea (e.g. cavity is the lung/s, e.g. cavity is the thoracic cavity). In some embodiments, there is no membrane between the natural orifice and the cavity, in which case, in some embodiments, a seal is introduced between the orifice and the cavity.

Although adjustable length cannulas are described in detail within this application it is to be understood that apparatus and/or methods described are, in some embodiments, used with a cannula of fixed length (e.g. without an extension). Where, for example, in some embodiments, a kit includes a plurality of different length cannulas and a cannula is selected based on patient anatomy dimension/s and/or the procedure to be performed.

An aspect of some embodiments of current invention relates to a method of providing access to a body cavity, for example, via a natural orifice. In some embodiments, access is provided to a body cavity through an outer skin incision e.g. laparoscopic surgery. For example, a cannula (e.g. a single lumen cannula) may be inserted entirely into the orifice and/or a distal end of the cannula may be inserted through an incision in a wall of the orifice into the body cavity.

Optionally, where the apparatus includes a cannula extension, a proximal extension to the cannula may be inserted into the orifice where a distal end of the extension is connected to the proximal end of the cannula. Additionally or alternatively, in some embodiments, a proximal end of the extension is accessible from outside the orifice. Optionally the orifice may be sealed around the proximal extension and/or the channel may be sealed.

In some embodiments, an incision may be supplied in a wall of an orifice, providing access to a body cavity. Optionally, the incision may be made by a surgical procedure. Optionally, the incision may be dilated to a desired shape and size. For example, the incision may be dilated to have dimensions similar to the distal cross section of the cannula.

In some embodiments, a cannula may have cross section similar to a cross section of a portion of the orifice (for example, at one or more dimensions of the maximum outer cross section of the cannula may range between 90 to 100 percent and/or 70 to 90 percent and/or 40 to 70 percent of corresponding dimensions of the smallest cross section of the orifice between the outer opening of the orifice and the incision). For example, the ratio of the a large dimension to a small dimension of cannula may range between 90 to 110 percent and/or between 70 to 130 percent and/or between 50 to 150 percent the ratio of the long dimension to the short dimension of a smallest cross section of the orifice between the outer opening to the incision in the wall to the body cavity. Optionally, a dilator may have a cross section and/or a ratio of long cross section dimension to short cross sectional dimension similar to the cannula. For example, ratio of long and short dimensions of the dilator and/or the cannula (and/or lumen/s of the dilator and/or cannula) cross section may range between 1.1 to 1.5 and/or between 1.5 to 3 and/or between 3 to 5. In some embodiments, a cross sectional dimension (e.g. width) of a lumen of the cannula (and/or sheath) is, in at least one dimension, a width of at least 21 mm or about 21 mm or a width of 5-50 mm, or 10-30 mm, or 15-25 mm, or lower or higher or intermediate dimensions or ranges.

In some embodiments, a cannula may be inserted through the orifice and/or into the cavity. Optionally, the cannula may be inserted entirely into the orifice. For example, a distal opening of the cannula may be inserted through the incision in the wall of the orifice into the cavity. For example, a proximal opening of the cannula may be positioned inside the orifice.

In some embodiments, the cannula may be stabilized inside the orifice. For example, the cannula may include a handle. The handle is optionally positioned protruding out of the orifice. For example stabilizing the cannula may include holding the handle and/or by mounting the handle to a support outside the orifice.

Additionally or alternatively, in some embodiments, the cannula is stabilized by connection to a connector where, in some embodiments, the connector includes a handle located outside the orifice. For example stabilizing the cannula may include holding the connector handle and/or by mounting the handle to a support outside the orifice. In some embodiments, the connector is coupled to a seal (e.g. including a GelPOINT® cap) sealing the orifice.

In some embodiments, a cutting device may be used to open an incision in a wall of the orifice and/or the cannula may be guided along the cutting device through the incision. Alternatively or additionally, a distal opening of cannula may be placed next to an incision location in the wall of the orifice and/or a cutting device may be inserted through the cannula to the incision site. For example the cutting device may include a needle and/or a laser and/or a blade and/or a dilator. Optionally the cutting device may be used to open an incision in the wall and then a distal portion of the cannula may be inserted through the incision.

In some embodiments, the cannula may be retained in the incision using the handle (e.g. cannula handle and/or connector handle). For example, there may be no other objects between the cannula and the sides of the incision. For example, there may no retainer inside the cavity (for example a retainer may include a ring and/or a widened lip of the cannula and/or a retractor). Alternatively or additionally, a retainer may be inserted into the incision. For example, the incision may not be sealed around the cannula. Alternatively or additionally, the incision may be sealed around the cannula.

In some embodiments, a proximal extension may be joined to a cannula. Optionally, a distal opening the extension may be joined to proximal opening of the cannula and/or a proximal opening of the extension may be in communication with an external opening of the orifice. For example, a proximal portion of the cannula may be inserted into a distal opening of the extension and/or a distal portion of the extension may be inserted into a proximal opening of the cannula. Alternatively or additionally a linking tube and/or a locking link and/or a flexible link may be used to join a proximal opening of the cannula to a distal opening of the extension.

In some embodiments, the length of a channel may be adjusted. For example, the extension may be inserted into the orifice until a proximal opening of the extension reaches a desired location. For example the proximal opening of the extension may be positioned approximately flush with an outer opening of the orifice. Alternatively or additionally, the proximal opening of the extension may be positioned protruding out of the orifice by a distance ranging between 1 to 5 cm and/or between 5 to 10 cm and/or between 10 to 50 cm. Alternatively or additionally, the proximal opening of the extension may be positioned inside the opening of the orifice by a distance ranging between 1 to 2 cm and/or between 2 to 5 cm and/or between 5 to 10 cm. Optionally the length may be adjusted while the lumen of the cannula remains in communication with the lumen of the extension. For example, the length of the channel may be adjusted be telescopic sliding of the extension with respect to the cannula.

In some embodiments, the orifice may be sealed around the channel. Optionally, the extension (or cannula in the case of apparatus with a fixed length cannula, or in the case of a telescoping cannula where the extension is part of the cannula) may be configured for sealing an opening of the orifice. For example, a sealing apparatus may be attached to the extension (or cannula). For example, in some embodiments, the sealing apparatus may include a sleeve and/or an access cap. Optionally the seal will preserve positive pressure in the orifice and/or the body cavity. For example, the pressure in the cavity may be greater than the external atmospheric pressure. Pressure in the orifice may be maintained at a positive pressure differential with respect to the external atmosphere by between 90 to 100 percent and/or between 70 to 90 percent and/or 40 to 70 percent and/or 10 to 40 percent as large as the pressure differential between the body cavity and the external atmosphere.

In some embodiments the seal on the orifice may allow access to the channel (and/or by means of the channel to the body cavity) and/or to the orifice. For example, a seal may include one or more ports to the channel and/or a seal may include one or more ports to the orifice (e.g. the space between an outer wall of the channel and an inner wall of the orifice). Optionally some or all of the ports may be sealable e.g. by a sealing element e.g. by a cap fitted to a proximal end of the port/s.

For example, using a port, an instrument may be inserted into the orifice and/or into the channel and/or through the channel into the cavity. In some embodiments, the sealing element (e.g. cap) forms a seal between the instrument and the port.

Alternatively or additionally, a gas and/or liquid may be introduced via a port into the orifice and/or into the channel and/or through the channel into the cavity.

In some embodiments, a handle of the cannula may pass through a port into the orifice. For example a proximal end of the handle may be passed through the seal and/or the seal may be positioned onto an opening of the orifice. Optionally, the seal (and/or a sealing element coupled to a port through which the handle passes) may provide a pressure seal around the handle and/or allow manipulation of the cannula.

An aspect of some embodiments of the current invention relates to supplying a pressure seal for a natural orifice and a channel through the orifice, where the channel provides access to a body cavity. In some embodiments, the channel includes a lumen of a cannula, e.g. a single lumen cannula. Optionally, the pressure seal will preserve a pressure differential between the orifice and/or channel and an outer atmosphere. In some embodiments there may be pressure communication between the cavity and the orifice and/or the cavity and the channel. Optionally the seal may preserve pressure in the orifice and/or the channel and/or the body cavity.

In some embodiments, there may be pressure and/or fluid (e.g. liquid and/or gas) communication between the channel and the orifice and/or between the orifice and the cavity and/or between the cavity and the channel. For example, an incision may allow communication between the body cavity and the orifice and/or between the body cavity and the channel. For example, the channel may include openings to the orifice and/or space between parts of the channel may allow communication between the channel and the orifice.

In some embodiments, there may be no active preservation of pressure differential between the channel and the body cavity. For example, there may be no active preservation of pressure differential between the channel and the orifice. For example, there may be no active preservation of pressure differential between the orifice and the body cavity. For example, there may not be a seal on the incision. For example, there may not be a seal between the cannula and the incision. For example, the walls of the channel may not be sealed against the orifice. Optionally, the pressure seal may preserve approximately equal pressure in the channel, the orifice outside the channel and/or the body cavity. For example, the pressure differential between the cavity and the outer atmosphere may be between 90 to 110 percent and/or between 80 to 120 percent and/or between 60 to 140 percent and/or between 30 to 200 percent the pressure differential between the orifice and the outer atmosphere. For example, the pressure differential between the cavity and the outer atmosphere may be between 90 to 110 percent and/or between 80 to 120 percent and/or between 60 to 140 percent and/or between 30 to 200 percent the pressure differential between the channel and the outer atmosphere. For example, the pressure differential between the channel and the outer atmosphere may be between 90 to 110 percent and/or between 80 to 120 percent and/or between 60 to 140 percent and/or between 30 to 200 percent the pressure differential between the orifice and the outer atmosphere. Optionally the pressure differential between the cavity and the outer atmosphere may range between 2 to 4 mm Hg and/or between 4 to 8 mm Hg and/or between 8 to 12 mm Hg and/or between 12 to 16 mm Hg and/or between 16 to 30 mm Hg. For example the pressure differential between the cavity and the outer atmosphere may be maintained via insufflation. For example, insufflation may be achieved by applying pressurized gas, for example air and/or Carbon Dioxide and/or Nitrogen.

Optionally in some embodiments a seal for an orifice (the seal, in some embodiments including a GelPOINT® cap) may include a port providing access from outside the orifice to the body cavity. For example a portion of a channel (e.g. extending from a distal face of the seal to the cavity) may pass through the seal. For example, a proximal opening of the channel may be exposed to an external atmosphere outside the seal (e.g. at a proximal face of the seal). Optionally there may be a cap for closing and/or limiting communication between the channel and the outer atmosphere.

Figure 2:
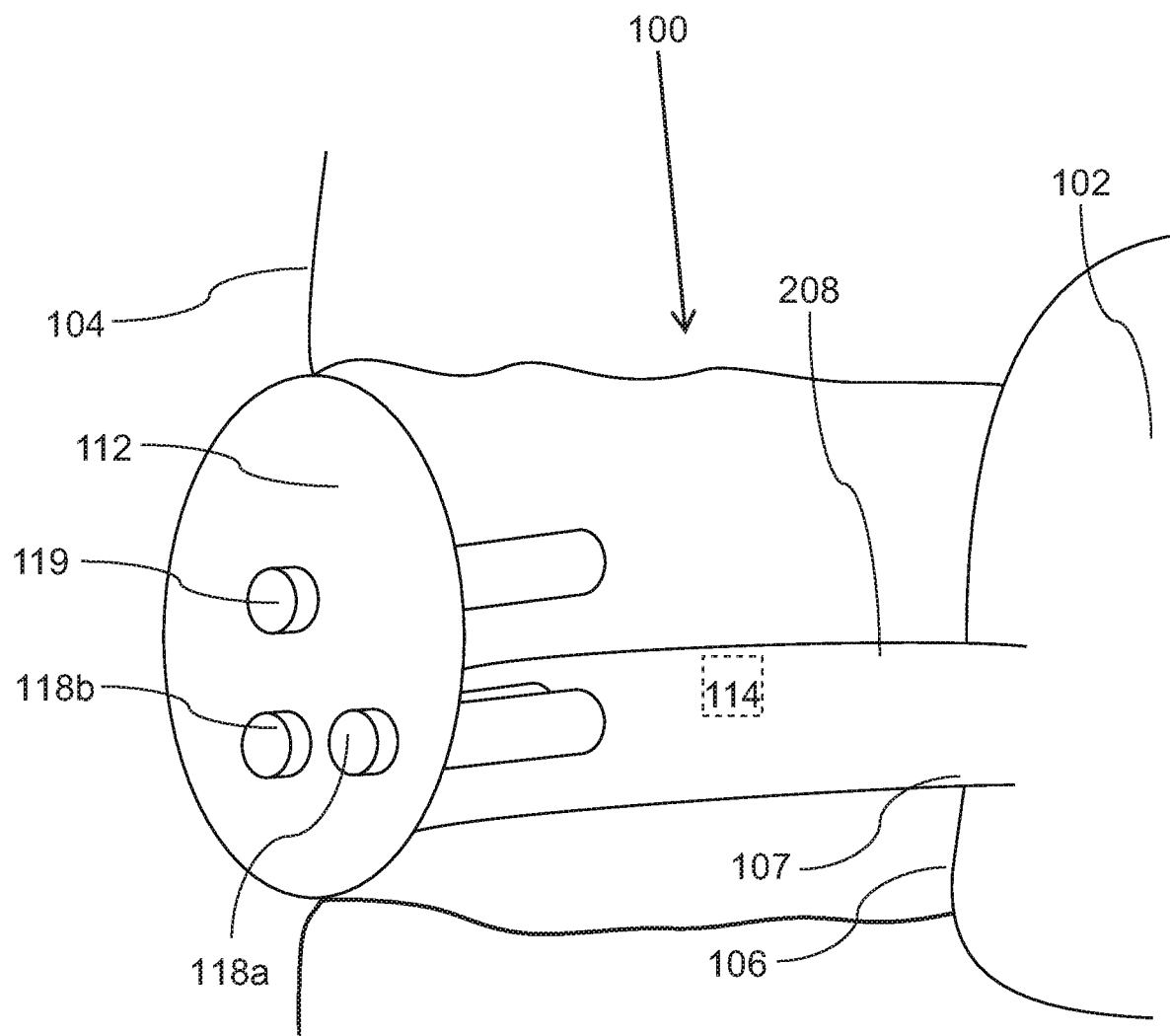
FIG. 2 is a schematic illustration of an access channel inserted through a natural orifice to a body cavity sealed to a natural orifice in accordance with embodiments of the current invention.

In some embodiments, access to the body cavity is supplied through the channel passing through the orifice. Optionally the channel includes a proximal opening outside of a sealed portion of the orifice. Optionally a cap is supplied to the proximal opening of the channel. For example, the cap may preserve pressure in the orifice and/or in the channel and/or in the body cavity. In some embodiments, the cap may include one or more openings (also herein termed "ports") e.g. providing access to the channel. The ports are optionally sized and shaped to allow entrance and/or seal around a tool, for example a catheter and/or endoscope and/or surgical mechanical arm (e.g. cylindrical surgical mechanical arm for example, including one or more feature of surgical arms described and/or illustrated in U.S. Pat. No. 10,022,197 and/or which is herein incorporated by reference in its entirety). In an exemplary embodiment, the cap includes one or more opening sized and/or shaped to allow entrance and/or seal around a cylindrical element of 1-20 mm, or 5-10 mm, or about 8 mm diameter, or lower or higher or intermediate ranges or diameters. Optionally multiple ports in the cap allow insertion of multiple tools into the channel for example as illustrated in FIGS. 2 and/or 6B and/or 8B and/or 13H-J.

Optionally, the channel may include one or more guides to guide a tool along the channel. In some embodiments, a port across the seal to the channel will be used for fluid communication.

In some embodiments, the cannula cross section has a long dimension and a short dimension where maximum widths (e.g. elastically relaxed widths) of the openings are smaller than the short dimension and a sum of the maximum widths (e.g. elastically relaxed widths) of the openings is smaller than the long dimension. Potentially, this means that surgical instruments which are inserted through the openings are suitably sized for insertion into the cannula. In some embodiments, this sizing of the openings and cannula potentially controls orientation of insertion of coupled surgical instruments. For example, in some embodiments, surgical arms coupled proximally (e.g. at motor units) in a linear configuration (e.g. in a row) are inserted through the openings where the orientation of the linear configuration through the cannula is controlled by the sizing of the openings.

In some embodiments, the seal includes one or more ports allowing access to the orifice. For example, a handle may pass through the seal between the orifice and the external atmosphere. For example, the handle may be used for stabilizing a portion of the channel and/or a distal opening of the channel and/or the incision. In some embodiments the port in the seal may supply access to the orifice outside the channel (for example for an instrument and/or for fluid communication).

In some embodiments, a port extends through most of the channel. For example, in some embodiments, a sheath including at least one lumen (e.g. a single lumen) extends through the sealing element through a portion of a length of the channel. Where the portion of the channel length is 50-99%, or 70-99%, or lower or higher or intermediate percentages or ranges. For example, in some embodiments, a long axis length of the sheath (and/or a portion of the sheath configured to extend distally from a distal face of the sealing element) is 50-99%, or 70-99%, or lower or higher or intermediate percentages or ranges of a long axis of the cannula (and/or a portion of the cannula configured to extend distally from the distal face of the sealing element).

In some embodiments, an access opening to the orifice e.g. through the seal is self-sealing, for example, closed when an instrument is not inserted through the opening. A potential benefit being that a pressure differential may be maintained by the seal when instrument/s are not inserted into the sea. For example, one or more port is self-sealing and/or sealable e.g. includes portions which elastically deform to allow insertion of an instrument e.g. include a duckbill seal e.g. a cannula seal e.g. one or more opening of a cap.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Variable Length Channel and Access Seal

FIG. 1 is a schematic illustration of a variable length channel inserted through a natural orifice in accordance with embodiments of the current invention.

In some embodiments, the channel may include multiple sections. Optionally, a distal section is open to a body cavity, for example through an incision in the wall of the orifice. Optionally an external opening of the orifice is sealed around a proximal portion of the channel. In some embodiments, the distal section of the channel is stabilized from outside the orifice.

In some embodiments, a channel 114 with proximal opening to outside a subject, passes through a natural orifice 100 and/or includes a distal opening 109 to a body cavity 102 of the subject. Optionally, a distal cannula 108 includes a distal opening 109 inserted through an incision 107 in the wall of orifice 100 to the body cavity 102. For example incision 107 may be made in tissue (e.g. a natural membrane) 106 (for example a rectovaginal septum separating the vagina from the recto uterine pouch. Optionally a proximal opening 105 of cannula 108 is positioned inside the orifice 100. Optionally, proximal opening 105 is in communication with a distal opening 115 of a proximal extension 110 of the channel 114. For example, the distal opening 115 of the extension 110 and the proximal opening 105 of the cannula may overlap. For example, the cannula 108 may slide telescopically inside the extension 110. Alternatively or additionally, the extension 110 may slide telescopically inside the cannula 108. Optionally, cannula 108 and/or extension 110 are rigid. Alternatively or additionally one or both of a cannula and/or an extension may be flexible with a fixed cross section. Alternatively or additionally one or both of a cannula and/or an extension may have a variable cross section. In some embodiments, a distal portion of cannula may be flexible while handle remain rigidly connected to the distal opening of the cannula.

Figure 9:
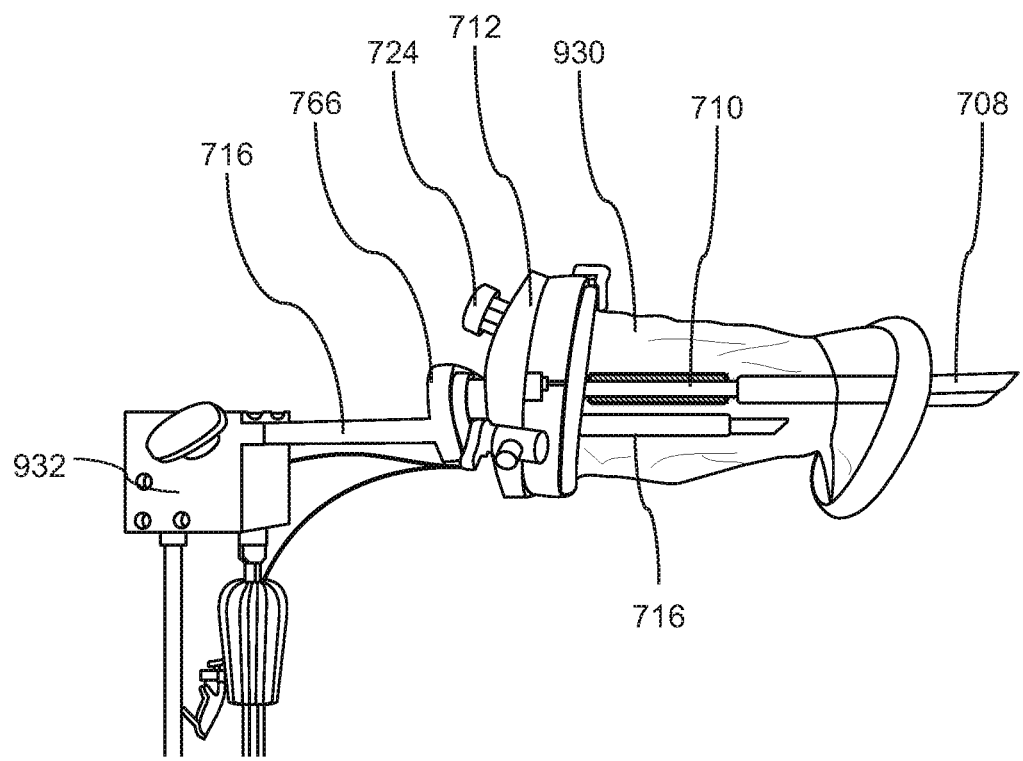
FIG. 9 is a photograph of a variable length channel and orifice seal connected to a support in accordance with embodiments of the current invention.

In some embodiments, cannula 108 is stabilized from outside the orifice. For example, cannula 108 may include a handle 116 that projects proximally beyond proximal opening 105. For example, handle 116 may project out beyond a seal 112 on the opening of the orifice 100. Optionally, handle 116 may be rigidly connected to cannula 108. Optionally, an external and/or proximal and/or protruding portion of handle 116 may be held by an operator and/or connected to an instrument holder (for example as illustrated in FIG. 9). For example, using handle 116 the distal opening 109 of cannula 108 may be held inside of cavity 102. Optionally, the cannula may not include a retaining mechanism (such as a retaining ring, a suture, a balloon and the like) to keep the distal opening of the cannula 108 inside cavity 102.

In some embodiments there may be fluid and/or pressure communication between the cavity and the orifice. For example, the cannula may be inserted directly through incision 107 and/or may not include a sealing mechanism separating cavity 102 from orifice 100. For example, the system may allow leakage of fluid and/or pressure between cavity 102 and orifice 100. Alternatively or additionally, the connection between cannula 108 and extension 110 may allow leakage of fluid and/or pressure between channel 114 and orifice 100.

Figure 6A:
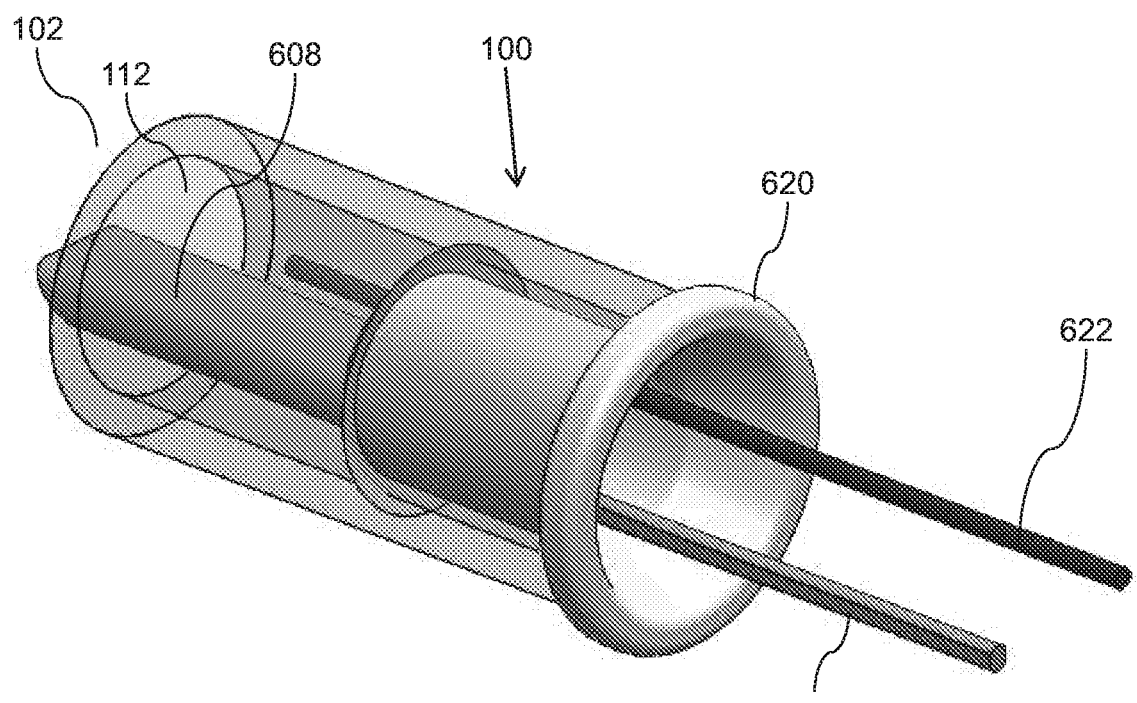
FIG. 6A is a schematic illustration of inserting a cannula into a natural orifice in accordance with embodiments of the current invention.
Figure 6B:
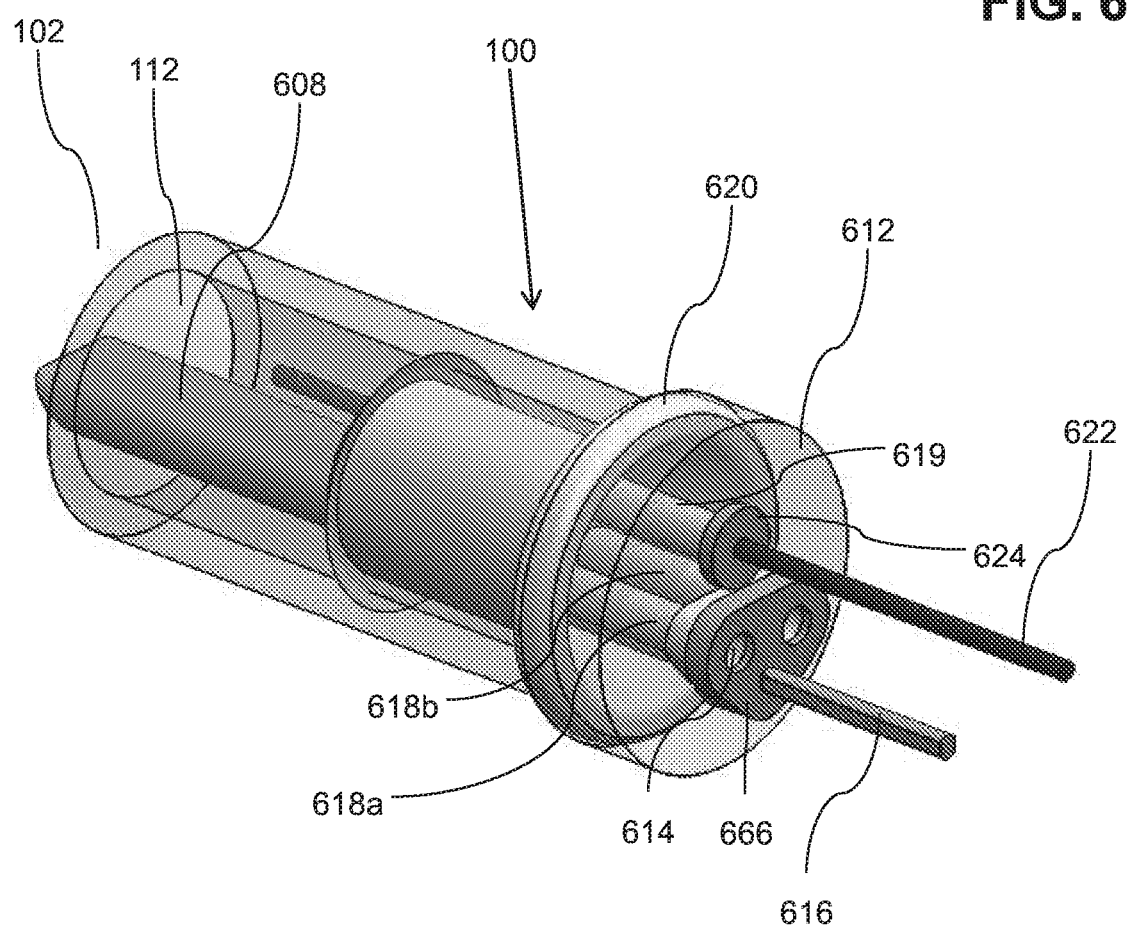
FIG. 6B is a schematic illustration sealing a channel to a natural orifice in accordance with embodiments of the current invention.
Figure 7:
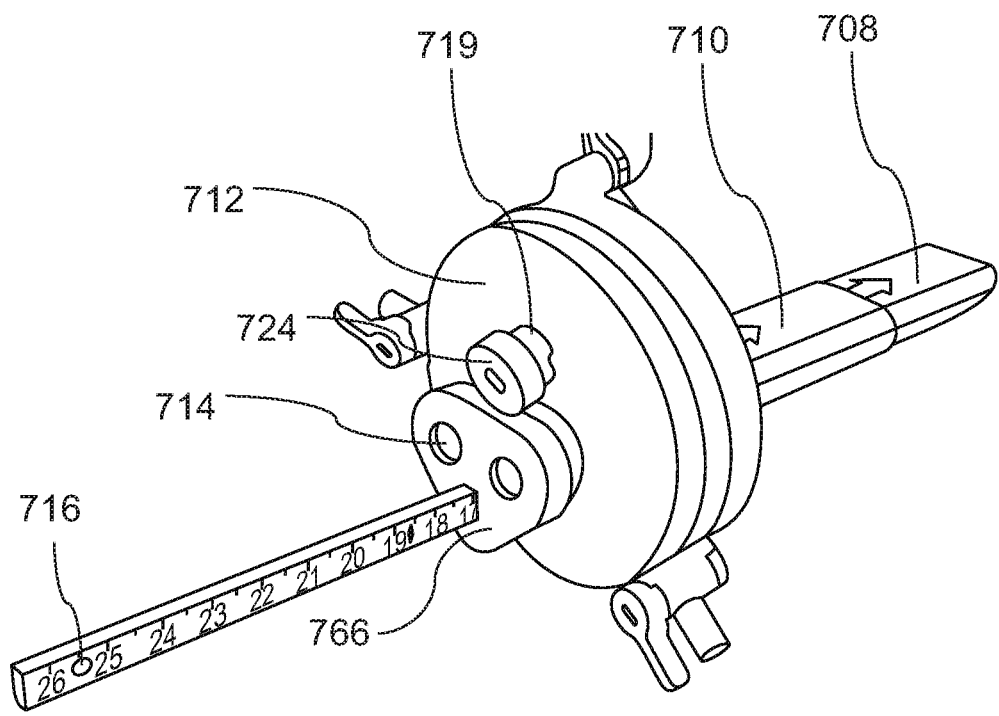
FIG. 7 is a photograph of a variable length channel and orifice seal in accordance with embodiments of the current invention.

In some embodiments, proximal section 110 of a channel 114 may include a seal 112. For example, seal 112 may be sized and shaped to seal orifice 100 around channel 114. For example, seal 112 may include a cap and/or a sleeve, for example as illustrated in FIGS. 6A, 6B and/or 9. Optionally, the seal may include one or more channels allowing access to the orifice, for example as illustrated in FIGS. 2 and/or 6B. For example, seal 112 may limit pressure and/or fluid communication between orifice 100 and an outer atmosphere. Optionally, a proximal opening 113 of channel 114 (which optionally includes a proximal opening of extension 110) may be exposed outside seal 112 and/or may supply access to channel 114 from outside the subject. Optionally, opening 113 may include a cap for example as illustrated in FIGS. 6B, 7 and/or 10. For example the cap may limits pressure communication and/or fluid between orifice channel 114 and an outer atmosphere.

In some embodiments, extension 110 is stabilized. For example, extension 110 may be stabilized by its connection to orifice 100, for example by seal 112. Alternatively or additionally, an extension may be connected to an external body part of the subject (for example skin 104). Alternatively or additionally, extension 110 may include a handle and/or be held by an operator and/or be connected to an instrument holder.

Figure 11:
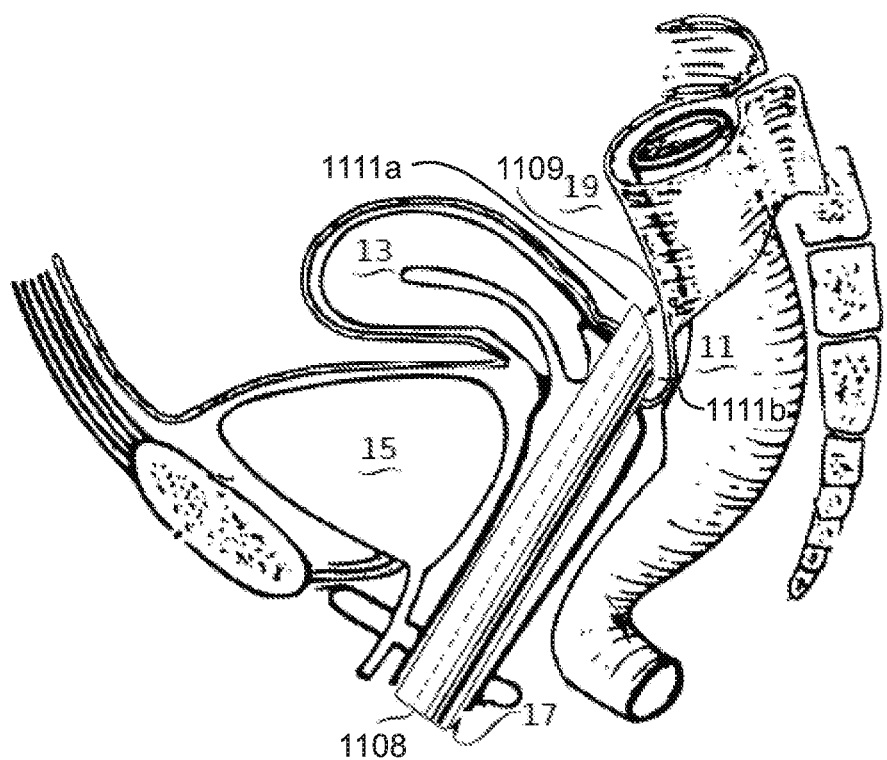
FIG. 11 is a schematic illustration of a channel inserted through a vagina into a pouch of Douglas in accordance with embodiments of the current invention.

In some embodiments, orifice 100 may include a lumen e.g. a vagina. Optionally, cavity 102 may include a pouch of Douglas and/or an abdominal cavity (for example as illustrated in FIG. 11).

FIG. 2 is a schematic illustration of an access channel inserted through a natural orifice to a body cavity and/or sealed to a natural orifice in accordance with embodiments of the current invention.

In some embodiments a seal 112 controls pressure and/or fluid exchanges between an external atmosphere and internal portions of a subject, for example channel 114, orifice 100 and/or cavity 102. In some embodiments, there may be free pressure and/or fluid communication between channel 114 and orifice 100. Alternatively, pressure and/or fluid communication between channel 114 and orifice 100 may be limited. In some embodiments, there may be free pressure and/or fluid communication between cavity 102 and orifice 100. Alternatively, pressure and/or fluid communication between cavity 102 and orifice 100 may be limited. In some embodiments channel 114 runs through a cannula 208. Optionally cannula 208 may have a variable length. For example, cannula 208 could include two telescoping parts (for example cannula 108 and/or extension 110 of FIG. 1). Alternatively or additionally, cannula 208 may include a single part with variable length, for example a bellows. Alternatively or additionally, cannula 208 may be flexible. Alternatively or additionally, cannula 208 may be rigid.

In some embodiments, an operator may keep a positive pressure in cavity 102. Optionally the pressure in cavity 102 will approximately equalize with the pressure in channel 114 and/or orifice 100.

In some embodiments, seal 112 may include one or more ports. Optionally, there may be one or more ports from outside the subject to orifice 100, for example port 119. Optionally, there may be one or more ports from outside the subject to channel 114, for example ports 118a and/or 118b. For example, ports 118a and/or 118b may allow insertion of multiple tools simultaneously into channel 114 and/or through channel 114 into cavity 102. Each port may include a cap and/or a seal. For example, each opening may be completely open and/or sealed around a tool and/or each opening may be completely sealed. Optionally a marker may show a length of channel 114.

Method of Accessing a Body Cavity Through an Orifice

Figure 3:
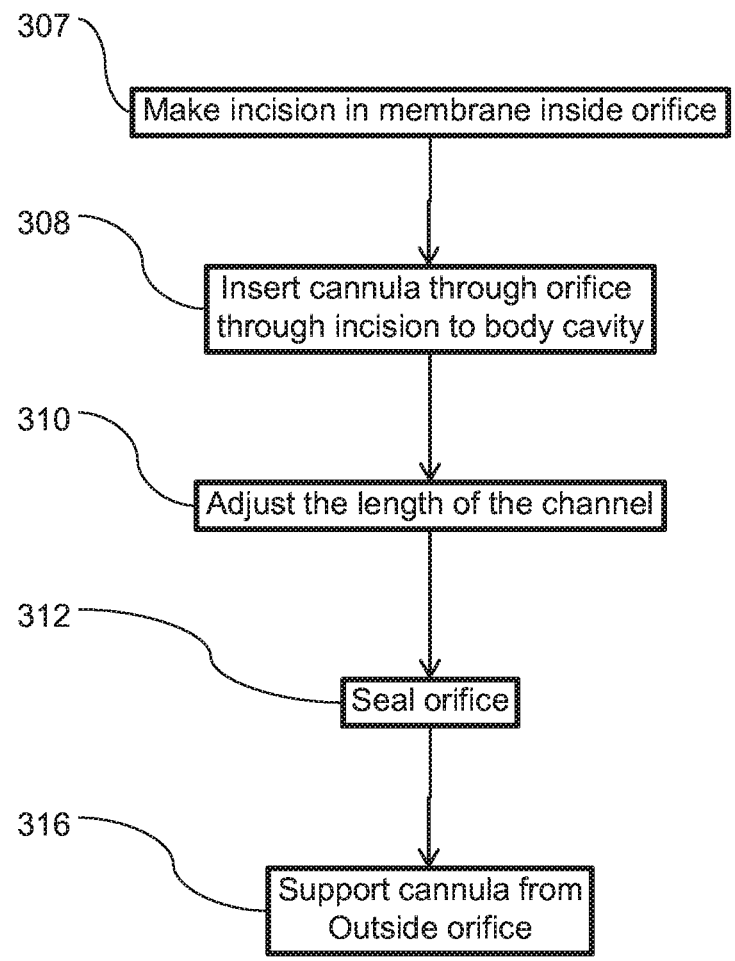
FIG. 3 is a flow chart illustration of a method of accessing a body cavity through a natural orifice in accordance with embodiments of the current invention.

FIG. 3 is a flow chart illustration of a method of accessing a body cavity through a natural orifice in accordance with embodiments of the current invention. In some embodiments a variable length channel is inserted through a natural orifice to a body cavity. Optionally, the orifice is sealed around the channel.

In some embodiments, the cavity may be insufflated. Optionally, insufflation may be achieved via a route other than orifice 110. Alternatively or additionally, insufflation may be achieved via orifice 110. Alternatively or additionally, cavity 102 may not be insufflated.

In some embodiments, an incision is made 307 between a natural orifice and a body cavity. For example, the incision may be made 307 in a wall of the orifice, for example in a membrane in the wall of the orifice. For example, the incision may be made 307 by first puncturing the wall and then expanding the puncture with one or more dilators. Alternatively or additionally, another method may be used to produce the incision. Alternatively or additionally, an opening between the orifice and the cavity be naturally occurring and/or have resulted from a pathological condition and/or remain from a previous procedure.

In some embodiments, a cannula may be inserted 308 into the orifice. For example, the cannula may include a distal portion of a channel that will supply access through the orifice to the cavity. Optionally, the cannula may be inserted 308 after making 307 the incision. For example, the cannula may be inserted 308 into the orifice until a distal portion of the cannula passes through the incision and/or until a distal opening of the cannula is positioned inside the cavity. Optionally a guide may be used to guide the cannula to the incision. For example, the cannula may fit around a dilator and/or the dilator may be used as a guide the cannula to the incision. Alternatively or additionally, the cannula may be inserted into the orifice before making 307 the incision. For example, the cannula may be positioned with a distal opening at an incision location and/or a needle and/or a dilator may be inserted through the cannula to make the incision.

In some embodiments, after insertion 308 of the cannula into the orifice, the length of the channel is adjusted 310. For example, the cannula may be shorted than the orifice. For example, the proximal end of the cannula may be located inside the orifice. Optionally, an extension is joined to a proximal opening of the cannula. For example, a lumen of the extension may be placed in communication with a lumen of the cannula. For existence, a distal opening of the extension may be joined to a proximal opening of the cannula. Optionally, the cannula and extension may move relative to one another to adjust 310 the length of the channel. For example, the cannula and extension may be connected telescopically for example as illustrated in FIG. 1. Alternatively or additionally, the channel may include an extendable element, for example a bellows. In some embodiments, the cannula may be extended to form a channel of the desired length. For example, with the distal opening of the channel inserted 308 through the incision, a proximal opening may reach an opening of the orifice (for example the length of the channel may be adjusted to be approximately equal to the length of the orifice). Alternatively or additionally, the cannula may be longer than necessary and/or the cannula may be contracted to the desired length. In some embodiments a length of the channel may be indicated, for example as illustrated in FIG. 7.

Figure 4:
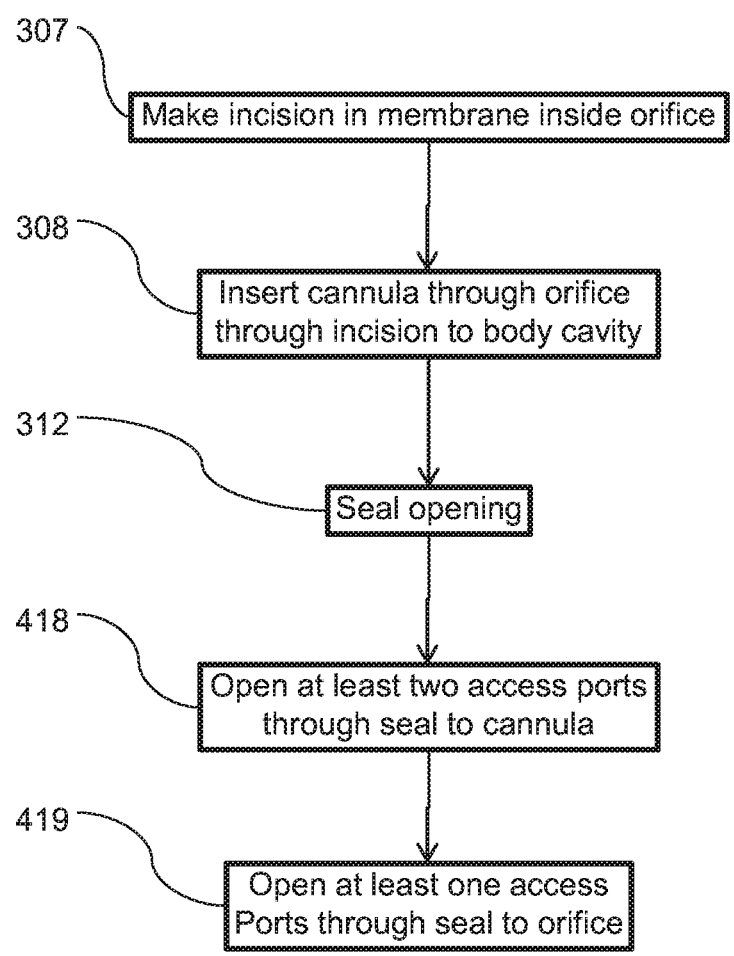
FIG. 4 is a flow chart illustration of a method of sealing a natural orifice access channel to body cavity in accordance with embodiments of the current invention.
Figure 5:
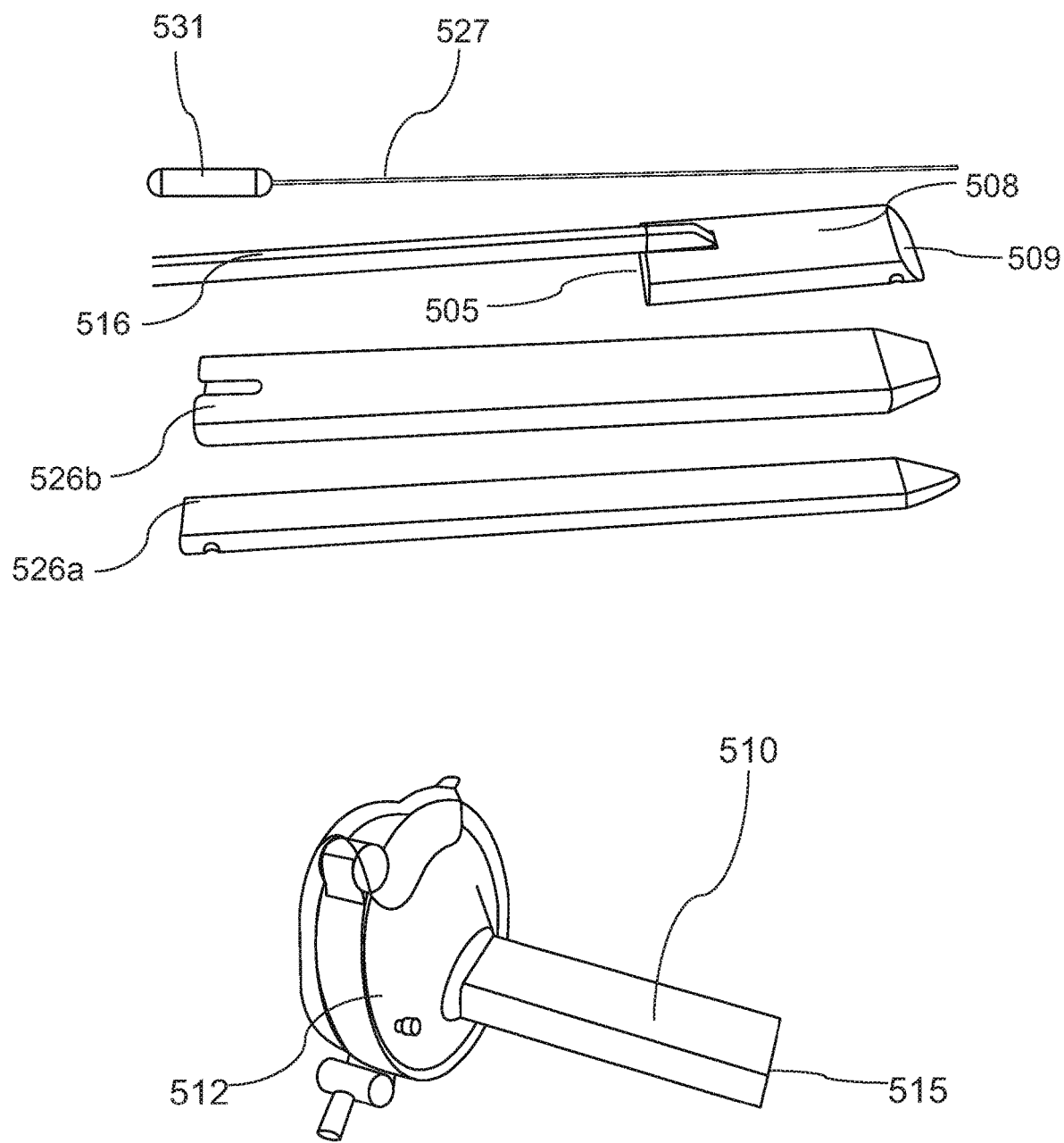
FIG. 5 is a photograph of components of an access channel to a body cavity in accordance with embodiments of the current invention.

In embodiments, the orifice may be sealed 312. Optionally, a seal may be attached to the channel for example as illustrated in FIGS. 1, 2, 5, 7 and/or 9. For example, the orifice may be sealed around the channel and/or the channel may be closed with a cap. Optionally one or more ports may be supplied to the orifice and/or to the channel, for example as illustrated in FIGS. 2, 4, 5 and/or 7. Optionally, the seal may control leakage of pressure from the cavity within the orifice. For example, the pressure between the cavity and/or the orifice and/or the channel may be equilibrated and/or a pressure difference between the cavity and/or the orifice and/or the channel and/or external atmosphere may be preserved.

In some embodiments, the cannula may be supported 316 from outside the orifice. For example, the cannula may include a handle that projects out from the orifice, for example as illustrated in FIGS. 1, 5, 6A and/or 6B. For example the handle may be supported 316 on an instrument holder, for example as illustrated in FIG. 9. Alternatively or additionally, the handle may be held by an operator. Optionally a seal may control communication of fluid and/or pressure around the handle. In some embodiments, the distal opening of the cannula may be stabilized inside the cavity by supporting 316 the cannula on an external support. Alternatively or additionally, there may be a retainer in the cavity for stabilizing the distal opening of the cannula inside the cavity. For example, one the cannula and/or the orifice seal is in place, the instrument holder may be aligned to the handle of the cannula. The handle is optionally then locked in place to the instrument holder.

Method of Sealing a Channel and/or an Orifice

FIG. 4 is a flow chart illustration of a method of sealing a natural orifice access channel to body cavity in accordance with embodiments of the current invention. In some embodiments, a channel may be supplied through a sealed orifice to a body cavity. Optionally one or more ports may supply access to the orifice and/or to the channel.

In some embodiments, an incision may be made 307 between the orifice and the cavity and/or a cannula inserted 308 into the orifice and/or an opening of the orifice may be sealed 312, for example as illustrated in FIG. 3.

In some embodiments one or more ports may be supplied 418, 419 through a seal to an orifice and/or to the channel. Optionally each port may seal independently to an instrument and/or may be separated sealable without an instrument. For example, a seal may include a gel closure. The ports may be cut into the closure. For example, a preshaped introducer may form ports in the closure, for example by puncturing the closure. Optionally an opening may be made with a non-circular shape. For example, the opening may be sized and shaped to fit the cross section of extension 510 for example as illustrated in FIG. 5 of extension 710 for example as illustrated in FIGS. 7 and/or 9.

In some embodiments, one or more ports may be supplied 418 to the channel. For example, a cross section of the cannel may include a long dimension and a short dimension. Multiple ports may be arranged along long dimension of the channel. For example, each tool may take up at substantially all off the short dimension of the channel cross section. For example, two instruments may fit side by side along the long le dimension of the cross section, but may not fit side by side along the short dimension.

In some embodiments, one or more access ports may be supplied 419 to the orifice. For example, a port through the seal to the orifice may include a port sized and shaped to fit a handle of a uterine manipulator. For example, a port through the seal to the orifice may include a port sized and shaped to fit the handle of the cannula, for example as illustrated if FIGS. 5, 6B, 7 and/or 10.

FIG. 5 is a photograph of components of an access channel to body cavity in accordance with embodiments of the current invention. In some embodiments, a cannula is shaped to fit into a natural orifice. Optionally, a dilator is shaped to fit through the cannula and/or to open an incision shaped and sized to fit a distal portion of the cannula. Optionally, a distal portion of an extension of the channel is made to fit a proximal portion of the cannula. Optionally, the extension includes a seal configured to limit pressure and/or fluid communication between the orifice and an external atmosphere.

In some embodiments, a cannula 508 is shaped to fit through a natural orifice. For example, cannula 508 has a wide flat cross section that fits a vagina. For example, cannula 508 has a cross section with a long dimension that is approximately twice its short dimension. Alternatively or additionally, the ratio of the long dimension to the short dimension may range between 1.1 to 1.6 and/or between 1.6 to 2.4 and/or between 2.4 to 3.0 and/or between 3.0 to 5.0. For example, for vaginal entry the long dimension of the cross section may range between 2 to 5 cm.

In some embodiments, cannula 508 includes a handle 516. Optionally, handle 516 extends proximally beyond a proximal opening 505 of the cannula. For example, handle 516 may extend proximally to proximal opening 505 a distance ranging between 0.5 to 1 and/or 1 to 2 times and/or 2 to 5 times the distance from proximal opening 505 to a distal opening 509 of the cannula. For example, handle 516 may be used to support cannula 508, for example as illustrated in FIGS. 3 and/or 9.

In some embodiments, a set of a first dilator 526a and/or a second dilator 526b are shaped to pass through cannula 508. For example, second dilator 526b may have dimensions that fit snugly through cannula 508. For example, the outer cross section of dilator 526b may range between 0.99 to 0.8 times and/or between 0.8 to 0.6 times the inner cross section of cannula 508. Optionally, first dilator 526a fits snugly into second dilator 526b. Optionally, a needle 527 and/or a needle holder 531 are supplied. For example, needle 527 fits through dilator 526a. For example, needle 527 may be used to puncture an initial incision in a wall of the orifice. Dilators 526a and/or 526b may be used successively to open the initial incision large enough to fit the distal portion of cannula 508 through the incision into a body cavity of a subject.

In some embodiments an extender 510 may be joined to cannula 508. For example, a distal opening 515 of extender 510 may be joined to proximal opening 505 of cannula 508 for example as illustrated in FIG. 1 and/or FIG. 3.

In some embodiments, extender 510 may be connected to a seal 512. For example, seal 512 may be shaped and sized to seal the orifice, for example as illustrated in FIGS. 1, 2, 3 and/or 4. Optionally, seal 512 may include ports opening to extender 510 and/or the orifice, for example as illustrated in FIGS. 1, 2, 3, 4 and/or 7. For example, multiple tools may fit side by side along the long dimension of the cross section of extension 510 and/or cannula 508.

FIG. 6A is a schematic illustration of inserting a cannula into a natural orifice in accordance with embodiments of the current invention. In some embodiments, a sleeve may be inserted into an opening of an orifice. Tools are optionally inserted through the opening to make an incision in a wall of the orifice. For example, the cannula may be inserted as illustrated in FIGS. 1, 3 and/or 9.

In some embodiments a sleeve 620 may be inserted into an orifice 100. For example, sleeve 620 may include a retractor and/or an anal port and/or a speculum. Optionally a cannula 608 may be inserted entirely (e.g. both a proximal opening and distal opening of cannula 608 may be inserted) into orifice 100. Optionally, a handle 616 may protrude out of the orifice 100 and/or be used to support the cannula 608. Optionally, a distal opening of the cannula 608 may be inserted into a body cavity 102 through an incision in a wall of the orifice. Optionally another tool 622, for example a tenaculum and/or a uterine manipulator may be inserted into orifice 100.

FIG. 6B is a schematic illustration of sealing a channel to a natural orifice in accordance with embodiments of the current invention. In some embodiments, a seal 612 may be fit to sleeve 620. Optionally seal 612 may limit pressure and/or fluid communication between orifice 100 and an outer atmosphere (for example as illustrated in FIGS. 1, 2 and/or 3). Optionally, seal 612 may include ports opening access to orifice 100 and/or cannula 608. For example a cap 666 may include two ports 618a and/or 618b including proximal openings 614 to a channel leading to cannula 608 and/or an incision and/or a body cavity 102. Using ports 618a and/or 618b two tools can independently be inserted through a single channel (e.g. cannula 608) and/or a single incision through orifice 100 and/or into cavity 102. Alternatively or additionally, cap 666 contains another port to orifice 100. For example handle 616 may protrude through the additional port. Optionally, a second cap 624 covers another port 619. For example, port 619 may serve for inserting tool 622 into orifice 100.

FIG. 7 is a photograph of a variable length channel and orifice seal in accordance with embodiments of the current invention. In some embodiments, a cannula is joined to extender to form a channel through an orifice. Optionally, the extender is connected to a seal for an opening of the orifice. A handle connected to the cannula optionally passes through the seal to support the cannula from outside the orifice for example as illustrated in FIGS. 1, 2, 3 and/or 4. Optionally, the handle is graduated. For example, the system of FIGS. 1, 2, 3, 4 and/or 7 may be used for transorifice laparoscopy.

In some embodiments, a cannula 708 is joined to an extender 710. For example together, the cannula and extender may form an access channel for transvaginal Culdoscopy. Optionally the extender 710 includes a seal 712. For example seal 712 limits pressure and/or fluid communication between the orifice and an outer atmosphere. For example seal 712 may be attached to extension 710, for example on a proximal portion thereof.

In some embodiments, extender 710 slides over cannula 708. Sliding of extender 710 over cannula 708 optionally telescopes (for example to extend or contract) a transvaginal access channel.

In some embodiments a handle 716 is connected to cannula 708. For example handle 716 extends proximally from cannula 708. Optionally, during use, handle 716 protrudes out seal 712 and/or is used to support cannula 708. In some embodiments, as cannula 708 slides with respect to extension 710, handle 716 slides with respect to seal 712.

In some embodiments, an indicator informs an operator of the length of the channel. For example, graduations are marked on handle 716. The graduations, for example, indicate the length of the access channel. For example, knowing the length of the access channel may assist an operator know how far to insert tools and/or dilators and/or may assist determine the proper placement of the cannula 708.

Optionally seal 712 includes one or more ports. Optionally, one or more ports are open to the orifice and/or the channel. For example, a port 719 may be open through seal 712 to the orifice. For example for culdoscopy, the orifice includes a vagina. For example port 719 may be used to control a uterine manipulator. Optionally a cap 724 limits pressure and/or fluid communication through port 719. Optionally multiple ports 714 may open to extension 710 and/or a channel through the orifice and/or a body cavity. Ports 714 are optionally used for independent access of multiple tools to a body cavity, for example a recto uterine pouch. In some embodiments, a cap 766 limits pressure and/or fluid communication between an outer atmosphere and/or the orifice and/or the channel. Optionally, seal 712 includes a further port to the orifice. For example, handle 716 passes through the port between the orifice and an external space. Optionally, cap 766 includes a slit through which handle 716 passes. For example the slit may limit pressure and/or fluid communication through the port and/or around handle 716.

Figure 8A:
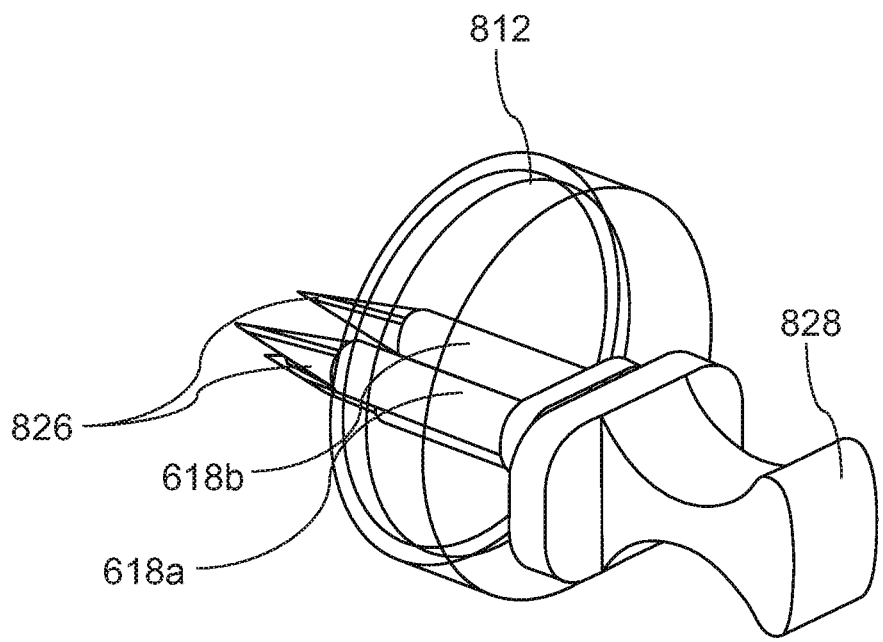
FIG. 8A is a schematic illustration of preparing an orifice seal in accordance with embodiments of the current invention.

FIG. 8A is a schematic illustration of preparing an orifice seal in accordance with embodiments of the current invention. For example, an introducer including dilators 826 may be used to poke one or more holes in a seal 812 and/or dilate and/or open existing hole/s. For example, the holes may include ports 618a and 618b and/or a third port into a seal 812. In some embodiments, a plurality of holes in seal 812 and/or two or more ports (e.g. two or more of ports 618a, 618b and the third port) are provided by a single port element. In some embodiments, a port element includes a single channel extending from a proximal face of the seal to a distal face of the seal (the channel is also termed "port"). In some embodiments, a port element includes a plurality of such channels or "ports".

For example ports 618a and 618b may provide access to a cross orifice channel. The third port may supply access to the orifice, for example for a handle of a cannula. In some embodiments, an introducer may include multiple dilators 826 and/or a handle 828. Optionally, the introducer may make multiple holes in a predefined pattern. For example, as illustrated in the figure, the introducer makes a set of three holes in a seal in a geometry suited for ports 714 to the trans orifice channel and/or the orifice and/or to form ports in a geometry that fit cap 766 and/or extender 710 and/or handle 716.

Figure 8B:
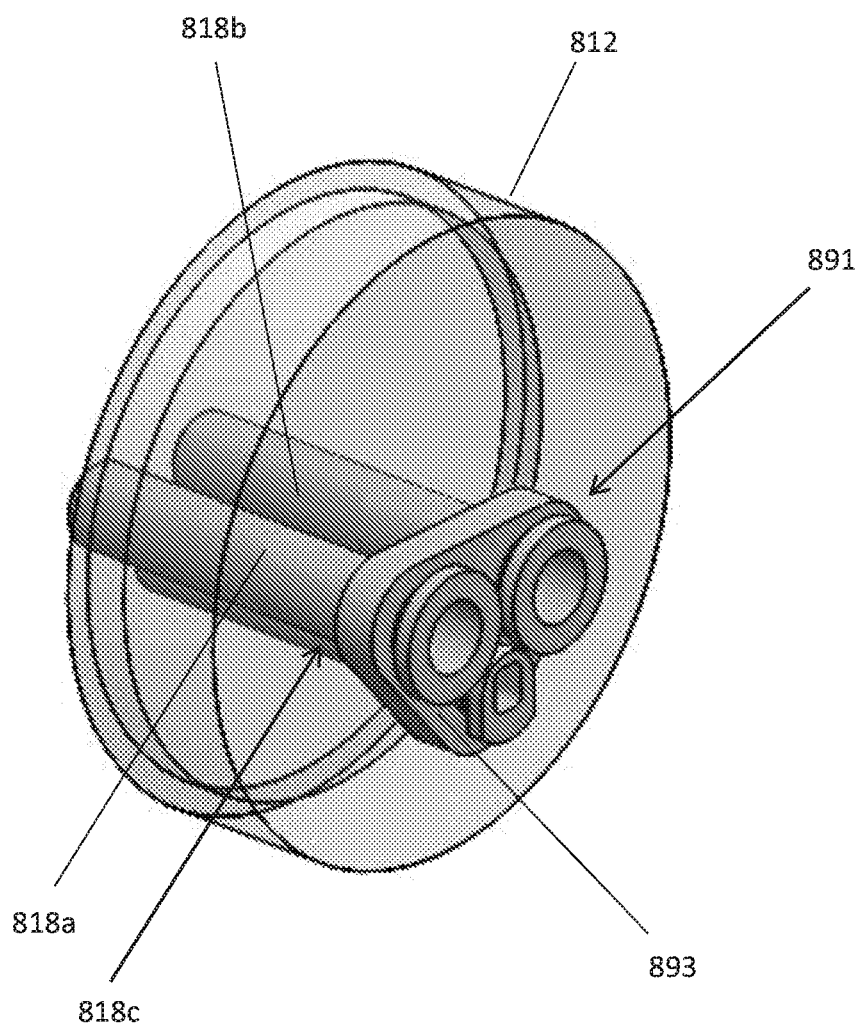
FIG. 8B is a simplified schematic of an orifice seal and a port element, according to some embodiments of the invention.

FIG. 8B is a simplified schematic of an orifice seal 812 and a port element 891, according to some embodiments of the invention. In some embodiments, port element 899 provides a plurality of channels through seal 812. For example, in some embodiments, port element includes ports 618a, 618b, 618c (port 618c also termed "the third port"). In some embodiments, port element 891 is a single piece. In some embodiments, port element 891 includes a base 893 which is configured (e.g. sized and/or shaped) to prevent ports from passing through seal 812. In some embodiments, base 893 connects one or more of ports 618a, 618b, 618c. In some embodiments, base 893 has at least one dimension perpendicular to an axis of a lumen of one or more of the ports which is larger than all cross sectional dimensions of one or more of the ports e.g. potentially preventing the port/s and/or port element from passing through seal 812. In some embodiments, the port element provides support and/or guidance to instrument/s inserted through the port element. In some embodiments, a handle connected to a cannula (e.g. handle 116 FIG. 1) extends through the third port, the port element thereby providing support to instrument/s inserted through one or more of ports 618a, 618b which is stabilized by the handle.

FIG. 9 is a photograph of a variable length channel and orifice seal connected to a support in accordance with embodiments of the current invention. Optionally, during use of an access system including a variable length channel, a distal portion of the channel may be held by a support.

In some embodiments, the channel and/or the orifice seal may be held by a support. Optionally, support 932 may be outside the subject. For example, handle 716 of cannula 708 is held by a support 932. Optionally, the subject is immobilized. For example, support 932 maintains a distal opening of cannula 708 inside a body cavity of the subject. For example, while held in the subject, the channel may be used for access to the cavity, for example for surgery.

In some embodiments, a sleeve 930 may be positioned in an entrance to an orifice, for example a vagina. Optionally sleeve 930 is attached to seal 712. For example, sleeve 930 may include a retractor, (for example an Alexis® wound retractor*). Seal 712 optionally includes an access cap (for example a GelPOINT® cap*) [* both available from Applied Medical 22872 Avenida Empresa, Rancho Santa Margarita, Calif. 92688]. In some embodiments, a distal end of sleeve 930 includes a base portion. In some embodiments the base portion is configured to anchor the sleeve inside the orifice. For example, in some embodiments, the base portion is sized and/or shaped to remain in position within the orifice e.g. elasticity of the orifice tissue holding the base portion in place. Alternatively or additionally, in some embodiments, the base portion includes a portion which is elastic, the portion being elastically compressed, positioned within the orifice and released, elastic forces of the base portion against the orifice tissue holding the base portion in place. In some embodiments, the base portion includes a reinforced ring which is, in some embodiments, elastic e.g. including silicone rubber. A potential advantage of the base portion is that it, in some embodiments, holds the sleeve in position and/or holds the sleeve open potentially preventing interference of the sleeve with other elements and/or provides sealing at the natural orifice.

In some embodiments, the channel is longer than sleeve 930. For example, a distal portion of cannula 708 may project longitudinally, past (and/or through) sleeve 930. For example, a distal portion of cannula 708 may project into a body cavity, for example through an incision in a wall of the orifice, for example into a recto urinary pouch.

Figure 10:
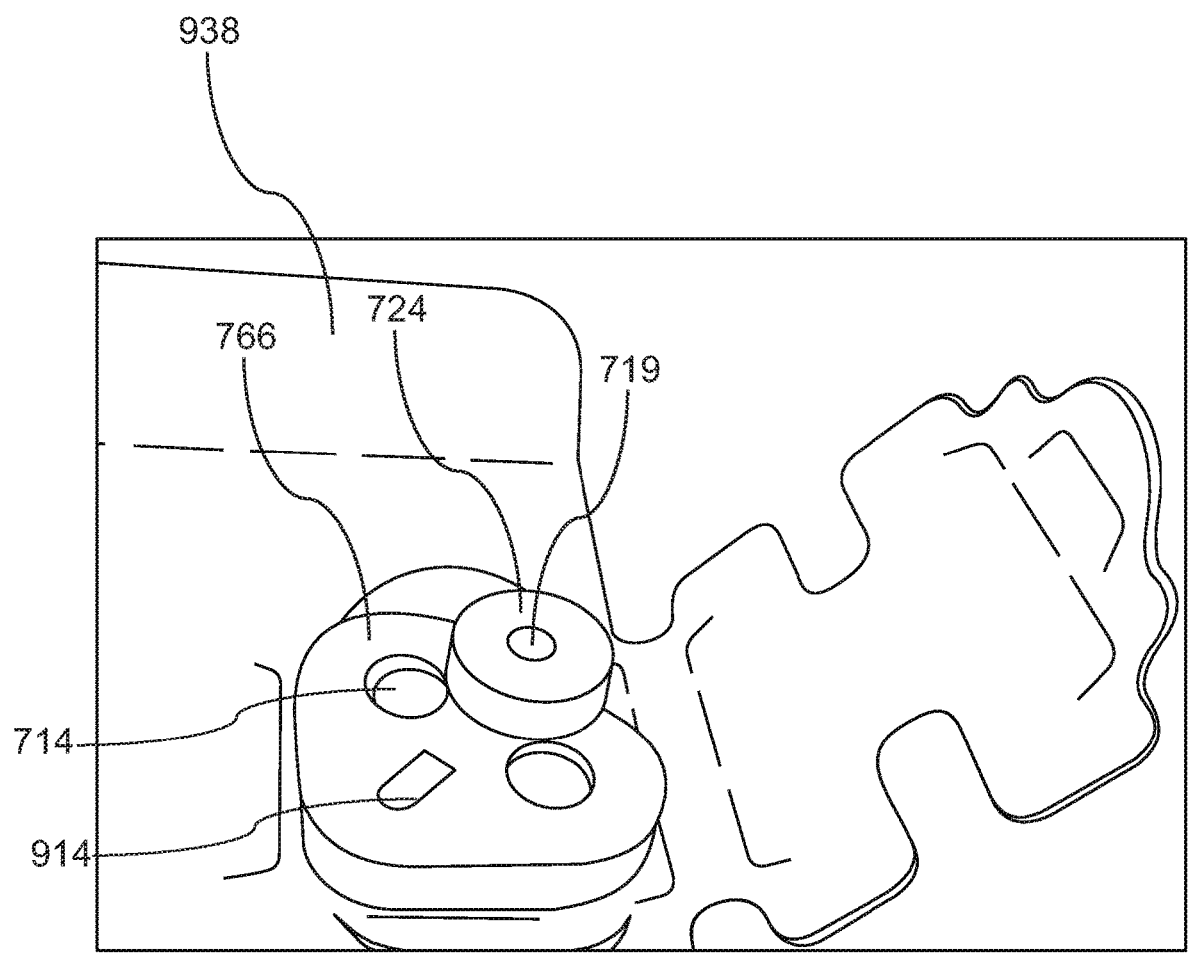
FIG. 10 is a photograph of an orifice seal end cap in accordance with embodiments of the current invention.

FIG. 10 is a photograph of an orifice seal end cap in accordance with embodiments of the current invention. For example two caps 724 and 766 are illustrated in a package 938 Optionally, cap 766 includes a slit 914. For example, slit 914 is sized and shaped fit to handle 716. For example, handle 716 may slide through slit 914. Additionally or alternatively, slit 914 may fit snugly to handle 716 and/or limit communication of pressure and/or fluid between the orifice and the outer atmosphere. Optionally the material of cap 766 (and/or cap 1325 FIGS. 13H-J) provides a pressure seal but has low friction to allow the sliding movement. In some embodiments, cap 766 (and/or cap 1325 FIGS. 13H-J) may be made of silicon or silicon with a friction reducing agent for example a coating of parylene.

FIG. 11 is a schematic illustration of a distal portion of a channel inserted through a vagina into a pouch of Douglas in accordance with embodiments of the current invention. In the exemplary embodiment, the channel passes through a natural orifice (e.g. a vagina 17) to provide access to a body cavity (e.g. a rectouterine pouch 19).

Reference is now made to FIG. 11, which schematically represents the positioning of cannula 1108 relative to anatomical structures of a female lower abdomen/pelvic region, according to some embodiments of the present disclosure. Among the anatomical structures shown are the uterus 15, vagina 17, bladder 15, rectum 11, and rectouterine pouch 19. Not shown are the handle (for example handle 116) of cannula 1108, and optional associated devices such as insufflation sealing which may be provided for, e.g., at the vaginal orifice, and/or a proximal extension (for example extension 110) which may be telescopically fitted to extend the length of cannula 1108.

In some embodiments, distal aperture 1109 of cannula 1108 is slanted at an angle between a leading distal-most edge portion 1111a, and a following, more proximal edge portion 1111b. The longitudinal distance between distal-most edge portion 1111a and proximal-most edge portion 1111b, in some embodiments, is about 15 mm. In some embodiments, the distance is about 10 mm, 12 mm, 14 mm, 16 mm, 18 mm, or another longer, shorter, or intermediate distance. A potential advantage of the slanting of distal aperture 1109 is to allow the cannula edge to be relatively retracted on an unprotected side of the cannula which could otherwise be accidentally positioned to scrape the rectum 11. As for the more-protruding leading-edge side of the aperture 1111b: (1) upon insufflation, tissue is generally lifted away from the rectum, reducing contact risk posed by this side, and (2) the robotic arms, where they exit the cannula, will generally be curved across the plane of the leading edge as they reach deeper into the peritoneal space. This potentially prevents contact of the leading edge with delicate internal tissues.

Additional Exemplary Embodiments

Figure 12:
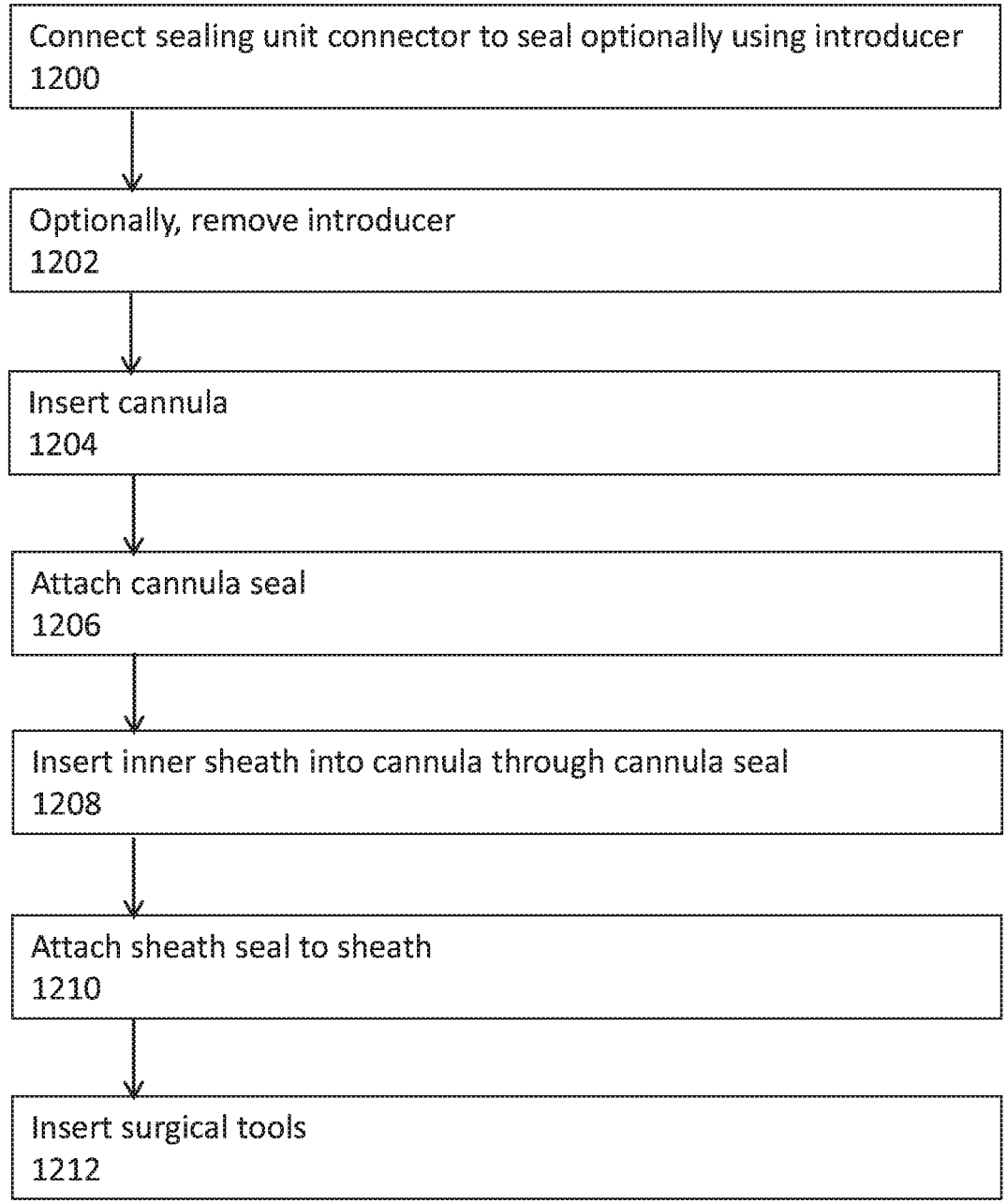
FIG. 12 is a flow chart illustration of a method of providing sealed access to body cavity through a sealed natural orifice and/or sealed channel, according to some embodiments of the invention.

FIG. 12 is a flow chart illustration of a method of providing sealed access to body cavity through a sealed natural orifice and/or sealed channel, according to some embodiments of the invention.

At 1200, in some embodiments, a sealing unit connector (e.g. connector 1318 FIGS. 13A-J) is coupled to a sealing element, also termed in this document "seal", (e.g. seal 1312 FIGS. 13A-J) which is sized and/or shaped to seal a natural orifice. In some embodiments, the sealing element includes a GelPOINT® cap. In some embodiments, coupling is by inserting at least a portion of the sealing unit connector into and/or through the seal, for example, by creating and/or opening and/or enlarging an opening in the seal and inserting at least a portion of the connector into and/or through the opening. In some embodiments, the seal includes flexible and/or elastic material which is configured to seal around the inserted connector.

Optionally, in some embodiments, insertion of the connector is using an introducer (e.g. introducer 1301 FIGS. 13A-J). Where, in some embodiments, force applied to the introducer is transferred to the seal to create and/or open and/or enlarge the opening in the seal and/or to insert one or more portion of the connector into and/or through the seal.

At 1202, optionally, in some embodiments the introducer is removed from the connector.

At 1204, in some embodiments a cannula (e.g. cannula 1310 FIGS. 13D, E, I and J) is inserted into the orifice and into the body cavity. In some embodiments, insertion is through the sealing element e.g. through a lumen in the connector coupled to the sealing element.

At 1206, in some embodiments, a cannula seal (e.g. cannula seal 1311 FIGS. 13E-G) is coupled to the cannula e.g. to a proximal end of the cannula which proximal end, in some embodiments, extends from a proximal face of the sealing element. In some embodiments, the cannula seal is coupled to a proximal end of the connector, sealing the connector lumen, connection between the connector lumen and the cannula being sufficiently close and/or including addition seal/s (e.g. an O-ring between the cannula and connector) so that the seal established between the connector and the cannula seal also seals the cannula.

At 1208, in some embodiments, an sheath (e.g. sheath 1323 FIGS. 13H-I) is inserted into the cannula through the cannula seal. In some embodiments, the sheath At 1210, in some embodiments, sheath seal, also termed "sheath cap" (e.g. sheath seal 1325 FIGS. 13H-J) is attached to a proximal opening of the sheath.

At 1212, in some embodiments, surgical instrument/s are inserted into the cavity through opening/s in the sheath cap. In some embodiments, a single surgical instrument is inserted into one or more sheath cap opening.

In some embodiments, the sheath cap provides a seal around the surgical instrument/s potentially maintaining a pressure differential between the cannula and pressure external to the cannula. In some embodiments, the presence of the cannula seal in addition to the sheath cap means that when there are no instruments and/or less instruments than sheath cap openings inserted through the cap, a pressure differential between the cannula lumen and entrance to the openings is maintained. For example, allowing removal and/or insertion and/or exchange of instruments during a procedure without losing pressure of the insufflated cavity.

FIGS. 13A-J are simplified schematics illustrating access and/or sealing apparatus, according to some embodiments of the invention.

Figure 13A:
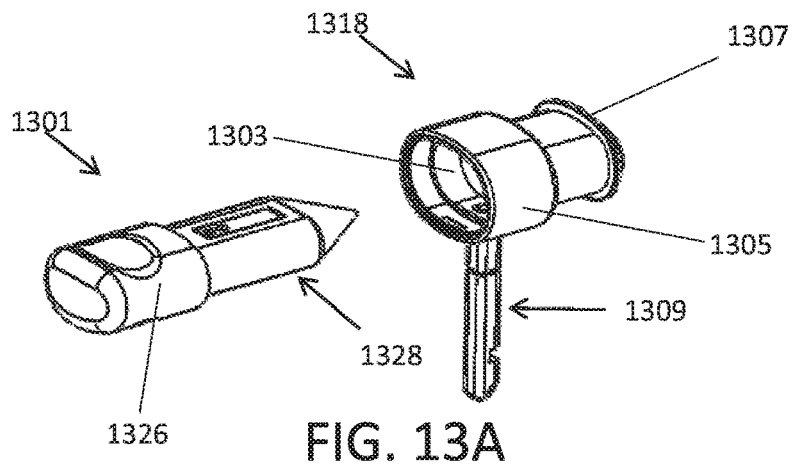
FIGS. 13A-J are simplified schematics illustrating access and/or sealing apparatus, according to some embodiments of the invention.

FIG. 13A shows an introducer 1301 and a sealing unit connector 1318, according to some embodiments of the invention.

In some embodiments, introducer 1301 includes a distal portion 1328 sized and/or shaped to fit into a lumen 1303 of sealing unit connector 1318. In some embodiments, distal portion 1328 of introducer 1301 includes a tapered dilator portion e.g. at a distal end of the introducer.

In some embodiments, introducer 1301 includes a handle 1326 e.g. at a proximal end of introducer 1310. In some embodiments, handle 1326 includes a portion which includes at least one cross sectional dimension which is larger than an entrance to sealing unit connector lumen 1303. Potentially, this enables force applied to handle to be transferred to connector 1318 e.g. so that a user applying force to the handle is able to push connector 1318 into and/or through a seal.

In some embodiments, connector 1318 includes a lumen 1303. In some embodiments, connector 1318 includes a rim (which is, for example, a flange) 1307 at a distal end of the connector lumen. In some embodiments, connector 1318 includes a rim (which is, for example, a flange) 1305 at a proximal end of the connector lumen 1303. In some embodiments, one or both of rims 1305, 1307 have a larger cross sectional dimension that a central portion of the connector. Potentially preventing movement of the connector out of the seal and/or through the seal.

In some embodiments, connector 1318 includes a support 1309 which, in some embodiments, is coupled to additional element/s e.g. to prevent movement of the connector e.g. with respect to other apparatus and/or a patient.

Figure 13B:
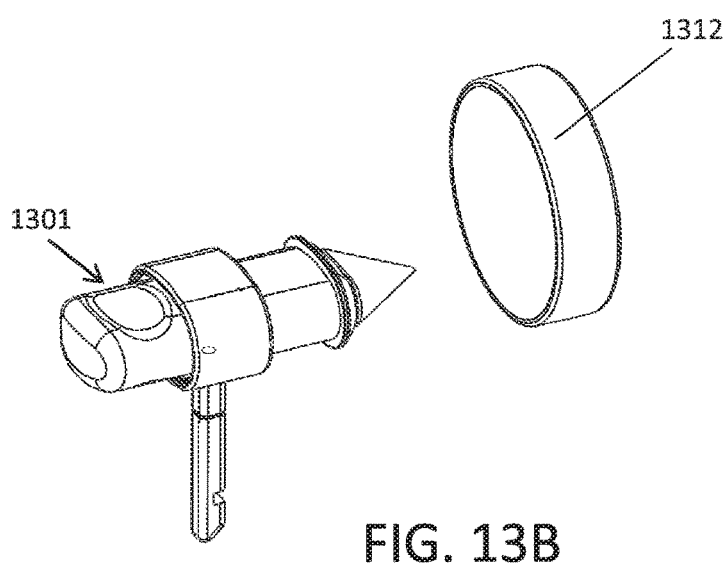

FIG. 13B shows introducer 1301 coupled to sealing unit connector 1318 and positioned in preparation for coupling to a seal 1312, according to some embodiments of the invention. Where coupling is, e.g. by insertion of a distal portion of the introducer into the lumen of connector 1318.

Figure 13C:
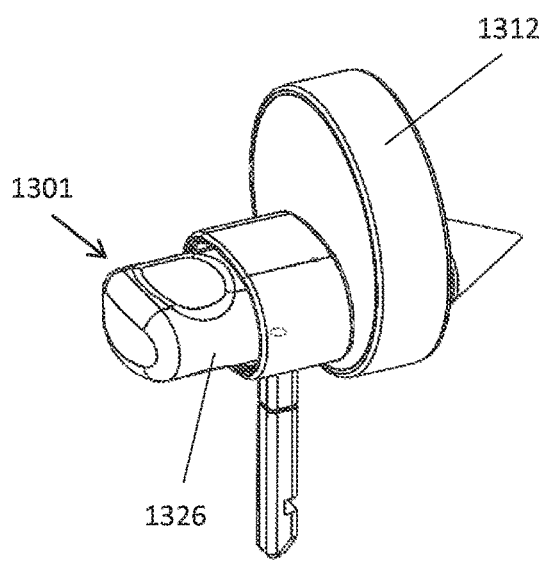

In some embodiments, FIG. 13C shows sealing unit connector 1318 coupled to seal 1312, achieved, for example, by application of pressure to handle 1301 until distal portion 1328 of the introducer pushes a distal portion of connector 1301 through into seal 1312 and/or a portion of connector 1310 through seal 1312. In some embodiments, introducer 1391 pierces a hole through seal 1312. Alternatively, in some embodiments, introducer 1391 enlarges an existing hole within seal 1312.

Figure 13D:
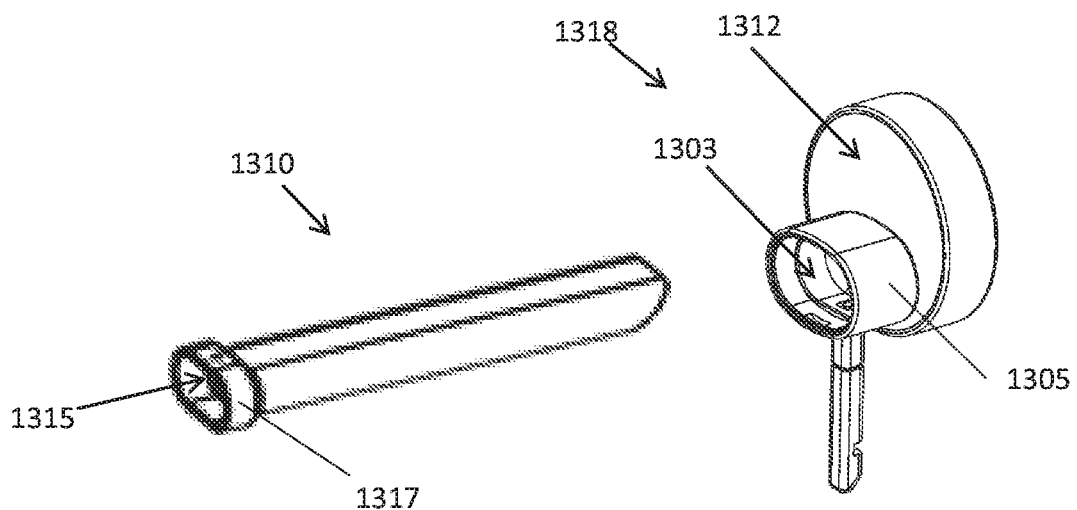

In some embodiments, FIG. 13D shows a cannula 1310 positioned for entrance into connector lumen 1303 which lumen forms a channel through seal 1312 (introducer 1301 has been removed from lumen 1303). In some embodiments, cannula 1310 has a single lumen 1315. In some embodiments, cannula 1310 has a rim (which is, for example, a flange) 1317 which, in some embodiments, is sized and/or shaped to be held by connector 1310 e.g. potentially preventing the cannula from passing entirely through lumen 1303 of connector 1318. In some embodiments, a cross section of rim 1317 includes one or more dimension which is larger than a cross sectional dimension of lumen 1303.

In some embodiments, cannula 1310 includes one or more features as described and/or illustrated regarding one or more of cannula 208 FIG. 2, 508 FIG. 5, 608 FIGS. 6A-B, 708 FIGS. 7, 9.

Figure 13E:
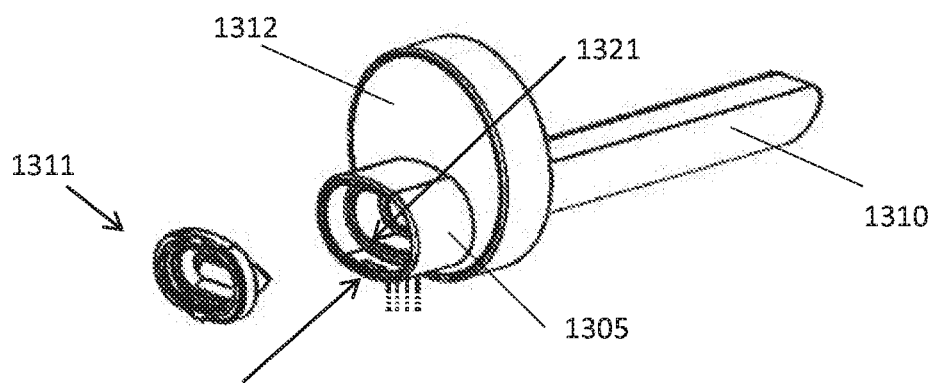

In some embodiments, FIG. 13E shows sealing unit connector 1318 and seal 1312 after cannula 1310 has been inserted through sealing unit lumen 1303 and a cannula seal 1311 orientated ready for attachment to proximal opening/s of the sealing unit and/or cannula. In some embodiments, a lumen cannula 1310, when connected to seal 1312 by connector lumen 1303 forms a lumen passing through a natural orifice (e.g. as described elsewhere in this document).

Figures 13F, 13G:
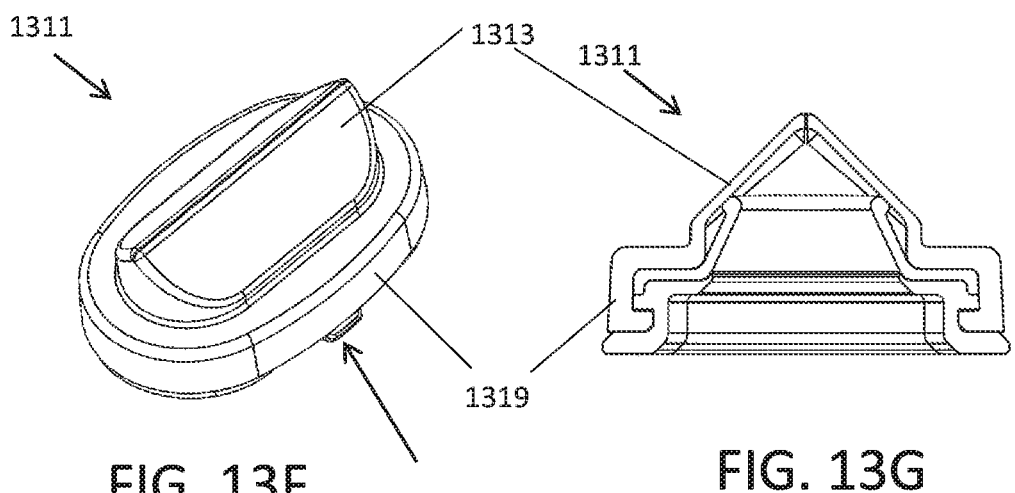

In some embodiments, FIG. 13F shows cannula seal 1311 and FIG. 13G shows a cross section of cannula seal 1311, according to some embodiments of the invention. In some embodiments, cannula seal 1311 includes a flexible portion 1313 sized and/or shaped to seal against a sheath (e.g. sheath 1315 FIGS. 13H-I). In an exemplary embodiment, flexible portion 1313 is a duckbill gasket with a direction of protrusion of the duckbill into lumen/s of the connector and/or cannula. In some embodiments, cannula seal 1311 includes a frame 1319. In some embodiments, frame 1319 is rigid. In some embodiments, cannula seal connects to the connector and/or cannula at the frame, which, in some embodiments, is sized and/or shaped to be held by a step 1321 between connector and cannula. Where, in some embodiments, step 1321 is present as a proximal end of the cannula is held recessed within connector lumen, a difference in size between the cannula and the connector generating the step. For example, as illustrated in FIG. 13E.

In some embodiments, cannula seal 1311 and/or connector 1305 include a connection geometry e.g. mating protrusion/s and/or indentations e.g. a snap-fit connection. In an exemplary embodiment, cannula seal 1311 includes a protrusion 1351 sized and/or shaped to fit into a notch 1353 in connector 1305. Potentially, such connection between the cannula seal 1311 and connector increases robustness of the connection e.g. potentially preventing loss in sealing provided by the cannula seal under use forces e.g. associated with insertion and/or removal of instruments e.g. associated with movement of the patient and/or of patient tissue.

Figure 13H:
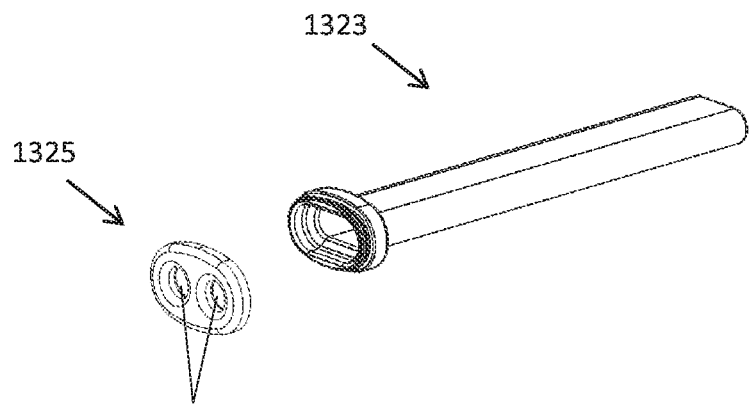

In some embodiments, FIG. 13H shows a sheath 1323 and a sheath seal 1325, also herein termed "sheath cap". In some embodiments, sheath seal includes a plurality of openings which, in some embodiments, are configured to each seal around a surgical tool. I For example, in some embodiments, one or more sheath seal opening is configured to seal against a surgical mechanical arm. In some embodiments, the sheath lumen and/or sheath seal and/or cannula seal and/or cannula lumen is sized and/or shaped to receive (e.g. simultaneously) two cylindrical elements (e.g. surgical mechanical arms) of 1-20 mm or 5-10 mm, or about 8 mm diameter or lower or higher or intermediate ranges or diameters. Where, in some embodiments, a space between the cylindrical elements is 0.5-20 mm or 0.5-10 mm or 1-5 mm, or about 5 mm, or less than 5 mm or lower or higher or intermediate distances or ranges. In some embodiments, a cross section of said single lumen (and/or of a lumen of the sheath) has a long dimension and a short dimension and each cap opening has a width smaller than the short dimension and the sum of the cap opening widths is greater than the short dimension and less than the long dimension, e.g. potentially controlling an angle of insertion of coupled surgical instruments.

In some embodiments sheath seal is formed of flexible material e.g. silicone rubber. In some embodiments, sheath seal 1325 includes one or more feature as described elsewhere in this document regarding cap/s, e.g. caps 624, 666 in FIG. 6B, caps 724, 766 in FIGS. 7, 9, and 10.

Figure 13I:
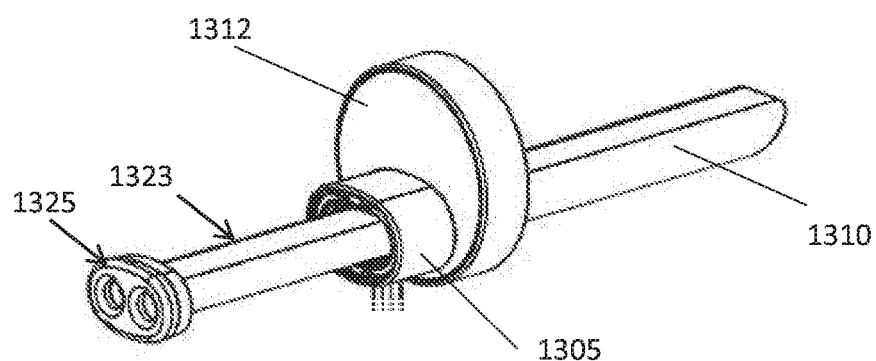

In some embodiments, FIG. 13I shows sheath seal 1325 coupled to sheath 1323 (e.g. a proximal end of sheath 1323) and sheath 1323 being inserted into cannula 1310. Where the sheath forms a channel through seal 1312 and, in some embodiments, to cannula 1310. In some embodiments, cannula seal 1311 is configured to make a seal between sheath 1323 and cannula 1311 and/or the lumen of connector 1305.

Figure 13J:
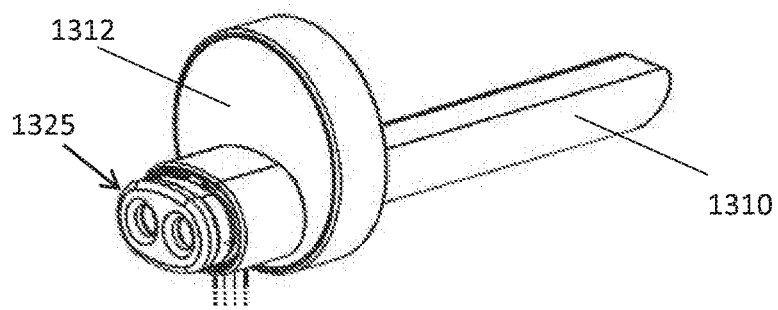

In some embodiments, FIG. 13J shows the sheath fully inserted into cannula 1310. In some embodiments, an opening in the sheath (e.g. at the distal end of the sheath) is disposed within cannula, for example, within a distal portion having 5%, or 10%, or 20% or 50% of a long axis length of the cannula. For example, in some embodiments, a long axis length of sheath is shorter than a long axis length of the cannula. For example, in some embodiments, a long axis length of the sheath is 50-99%, or 80-99% or 80-99% of a long axis length of the cannula. In some embodiments, the sheath and the cannula have substantially the same long axis length e.g. within 1 mm, or 10 mm, or 20 mm of a distal end and/or opening of the cannula.

General

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An access port for sealing an opening of a natural orifice and supplying access to a body cavity through the natural orifice comprising:
    a sealing unit;
    an unobstructed single lumen cannula extending to said body cavity;
    a connector connecting said cannula to said sealing unit; said connector comprising a connector lumen which defines an access opening through the sealing unit to said single lumen; wherein said connector lumen comprises proximal and distal openings, said proximal opening disposed proximal to a proximal face of said sealing unit, said distal opening disposed distal of a distal face of said sealing unit; and
    a cap including a plurality of cap openings configured to seal between medical instruments inserted into said cap openings and said access opening.

2. The access port of claim 1, wherein one or both of proximal and distal openings of said connector has a flange.

3. The access port of claim 1, comprising an opening through said sealing unit to the natural orifice.

4. The access port of claim 1, wherein said natural orifice is a vagina.

5. The access port of claim 1, wherein said cannula is open to an intraperitoneal cavity through said natural orifice.

6. The access port of claim 1, comprising a sheath extending from a proximal face of said sealing unit, through said sealing unit and through to said cannula lumen and extending within at least a portion of a length of said cannula lumen.

7. The access port of claim 6, comprising a cannula seal configured to seal one or both of a proximal opening of said cannula and a proximal opening of said sheath.

8. The access port of claim 1, comprising a port element describing a channel through said sealing unit and opening to said cavity.

9. The access port of claim 1, comprising a port element describing a channel through said sealing unit and opening into said lumen of said cannula.

10. The access port of claim 9, wherein said port element includes a sheath extending from a proximal face of said sealing unit, through said cannula and extending within a least a portion of said cannula.

11. The access port of claim 1, wherein a transverse cross section of said single lumen has a long dimension and a short dimension; and
    wherein each of said cap openings has a width smaller than said short dimension and the sum of widths of said plurality of cap openings is greater than said short dimension and less than said long dimension.

12. The access port of claim 11, wherein said cross section of said single lumen has, in at least one dimension, a width of at least 21 mm.

13. The access port of claim 1, wherein a transverse cross section of said single lumen has a long dimension and a short dimension, and at least one of said openings has a width at least 90% the short dimension.

14. A kit for providing access to a cannula leading to a body cavity through a seal on a natural orifice comprising:
    a connector comprising:
        a channel with a distal opening and a proximal opening, said channel configured to pass through said seal and attach to a cannula passing through the orifice to the body cavity, said connector having a distal opening on an inner side of said seal and a proximal opening on an outer side of said seal;
    a cap comprising a plurality of openings and sized and shaped to seal a lumen of said cannula;
    a sheath sized and shaped to pass through said connector and extend within at least a portion of said cannula lumen; and
    a sealing element sized and shaped to fit to one or both of said sheath and said cannula and including elastically bendable flexible portions which, when elastically relaxed, close a lumen of said sealing element to seal one or both of said sheath and said cannula.

15. The kit of claim 14, wherein said cap is sized and shaped to attach to one or more of a proximal opening of said cannula, a proximal opening of said sheath, and a proximal opening of said connector.

16. The kit of claim 14, wherein said distal opening of said connector has a cross section with a long dimension and a short dimension and wherein said long dimension is at least twice said short dimension.

17. The kit of claim 14, further comprising an introducer for insertion of said connector into or through said seal, said introducer including a handle at a proximal portion of said introducer and a distal portion shaped and sized to fit into said channel of said connector; wherein said handle comprises a portion which is larger than an entrance to said channel of said connector.

18. The kit of claim 17, wherein said distal portion of said introducer comprises a tapered portion.

19. The kit of claim 14, wherein said cap comprises a duckbill gasket defining a protrusion in the direction of said cannula.

* * * * *